United States Patent
Hasenberg et al.

(10) Patent No.: US 12,402,899 B2
(45) Date of Patent: Sep. 2, 2025

(54) SYSTEMS, DEVICES, AND METHODS FOR GENERATING SHOCK WAVES IN A FORWARD DIRECTION

(71) Applicant: Shockwave Medical, Inc., Santa Clara, CA (US)

(72) Inventors: Thomas Charles Hasenberg, Campbell, CA (US); Rainier Betelia, San Jose, CA (US); Michael Lang, Woodbury, MN (US); Jason B. Franco, Milpitas, CA (US); Robert Zelenka, Milpitas, CA (US); Thu Anh Ho, San Jose, CA (US); Todd Weston Jenkins, San Jose, CA (US); Andrew James Hudon, Tabernash, CO (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 19 days.

(21) Appl. No.: 18/524,575

(22) Filed: Nov. 30, 2023

(65) Prior Publication Data

US 2025/0176984 A1    Jun. 5, 2025

(51) Int. Cl.
*A61B 17/22*    (2006.01)
*A61M 5/00*    (2006.01)
(Continued)

(52) U.S. Cl.
CPC ............ *A61B 17/22012* (2013.01); *A61B 2017/00137* (2013.01); *A61B 2017/00292* (2013.01);
(Continued)

(58) Field of Classification Search
CPC .... A61B 17/22012; A61B 2017/00137; A61B 2017/00292; A61B 2017/00982; A61B 2017/22021; A61B 2218/007
See application file for complete search history.

(56) References Cited

U.S. PATENT DOCUMENTS 2,916,647 A    12/1959    George
3,412,288 A    11/1968    Ostrander
(Continued)

FOREIGN PATENT DOCUMENTS

AU    2009313507 B2    11/2014
AU    2013284490 B2    5/2018
(Continued)

OTHER PUBLICATIONS

Latanich et al., (2023). "Shockwave Intravascular Lithotripsy Facilitated Transvenous Lead Extraction," JACC Clin Electrophysiol, 9(8 Pt 2):1585-1592.
(Continued)

*Primary Examiner* — Julian W Woo
(74) *Attorney, Agent, or Firm* — Morrison & Foerster LLP

(57) ABSTRACT

An exemplary catheter for use in a body lumen comprises: a catheter body; and a plurality of shock wave emitters disposed at a distal end of the catheter body, each shock wave emitter configured to generate a shock wave that propagates distally of the catheter body, wherein the plurality of shock wave emitters are arrayed about a longitudinal axis of the catheter body such that shock waves emitted from the plurality of shock wave emitters can constructively interfere distally of the catheter body, and wherein each shock wave emitter comprises electrodes separated by a spark gap and at least one electrical connector that connects at least one of the electrodes to an electrode of another shock wave emitter of the plurality of shock wave emitters.

61 Claims, 15 Drawing Sheets

(51) Int. Cl.
*A61M 25/10* (2013.01)
*A61B 17/00* (2006.01)

(52) U.S. Cl.
CPC ............ *A61B 2017/00681* (2013.01); *A61B 2017/00982* (2013.01); *A61B 2017/22021* (2013.01); *A61B 2218/007* (2013.01)

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 | 3/2009 | Eggers et al. |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Hakala et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,238,405 B2* | 3/2019 | Cioanta ............... A61B 17/225 |
| 10,499,892 B2* | 12/2019 | Sotak ............... A61B 17/12109 |
| 10,517,620 B2 | 12/2019 | Adams |
| 10,517,621 B1 | 12/2019 | Adams |
| 10,555,744 B2 | 2/2020 | Nguyen et al. |

(56) References Cited

U.S. PATENT DOCUMENTS

| | | |
|---|---|---|
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,026,707 B2 * | 6/2021 | Ku .................... A61B 17/2202 |
| 11,076,874 B2 | 8/2021 | Hakala et al. |
| 11,337,713 B2 | 5/2022 | Nguyen et al. |
| 11,432,834 B2 | 9/2022 | Adams |
| 11,478,261 B2 | 10/2022 | Nguyen |
| 11,534,187 B2 | 12/2022 | Bonutti |
| 11,596,423 B2 | 3/2023 | Nguyen et al. |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 11,779,363 B2 | 10/2023 | Vo |
| 12,048,445 B2 | 7/2024 | Mantell |
| 12,076,082 B2 * | 9/2024 | Fanier .................... A61B 18/26 |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2019/0150961 A1 | 5/2019 | Tozzi |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2022/0265295 A1 | 8/2022 | McCaffrey et al. |
| 2023/0043475 A1 | 2/2023 | Adams |
| 2023/0107690 A1 | 4/2023 | Nguyen |
| 2023/0165598 A1 | 6/2023 | Nguyen et al. |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| CN | 114903558 A | 8/2022 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2011520248 A | 12/2004 |
| JP | 2005501597 A | 1/2005 |

(56) References Cited

FOREIGN PATENT DOCUMENTS

| | | | |
|---|---|---|---|
| JP | 2005095410 A | 4/2005 |
| JP | 2005515825 A | 6/2005 |
| JP | 2006516465 A | 7/2006 |
| JP | 2007289707 A | 11/2007 |
| JP | 2007532182 A | 11/2007 |
| JP | 2008506447 A | 3/2008 |
| JP | 2011513694 A | 4/2011 |
| JP | 2011524203 A | 9/2011 |
| JP | 2011528963 A | 12/2011 |
| JP | 2012505050 A | 3/2012 |
| JP | 2012508042 A | 4/2012 |
| JP | 2015525657 A | 9/2015 |
| JP | 2015528327 A | 9/2015 |
| JP | 6029828 B2 | 11/2016 |
| JP | 6081510 B2 | 2/2017 |
| WO | WO-1989011307 A1 | 11/1989 |
| WO | WO-1996024297 A1 | 8/1996 |
| WO | WO-1999000060 A1 | 1/1999 |
| WO | WO-1999002096 A1 | 1/1999 |
| WO | WO-2000056237 A2 | 9/2000 |
| WO | WO-2004069072 A2 | 8/2004 |
| WO | WO-2005099594 A1 | 10/2005 |
| WO | WO-2005102199 A1 | 11/2005 |
| WO | WO-2006006169 A2 | 1/2006 |
| WO | WO-2006127158 A2 | 11/2006 |
| WO | WO-2007088546 A2 | 8/2007 |
| WO | WO-2007149905 A2 | 12/2007 |
| WO | WO-2009121017 A1 | 10/2009 |
| WO | WO-2009126544 A1 | 10/2009 |
| WO | WO-2009136268 A1 | 11/2009 |
| WO | WO-2009152352 A2 | 12/2009 |
| WO | WO-2010014515 A2 | 2/2010 |
| WO | WO-2010054048 A2 | 9/2010 |
| WO | WO-2011006017 A1 | 1/2011 |
| WO | WO-2011094111 A2 | 8/2011 |
| WO | WO-2011143468 A2 | 11/2011 |
| WO | WO-2012025833 A2 | 3/2012 |
| WO | WO-2013059735 A1 | 4/2013 |
| WO | WO-2014025397 A1 | 2/2014 |
| WO | WO-2014025620 A1 | 2/2014 |
| WO | WO-2015017499 A1 | 2/2015 |
| WO | WO-2019099218 A1 | 5/2019 |

OTHER PUBLICATIONS

International Search Report and Written Opinion received for International Patent Application No. PCT/US2023/082079 mailed on Oct. 11, 2024, 14 pages.

Invitation to pay additional fees received for International Patent Application No. PCT/US2023/082079 mailed on Aug. 12, 2024, 3 pages.

* cited by examiner

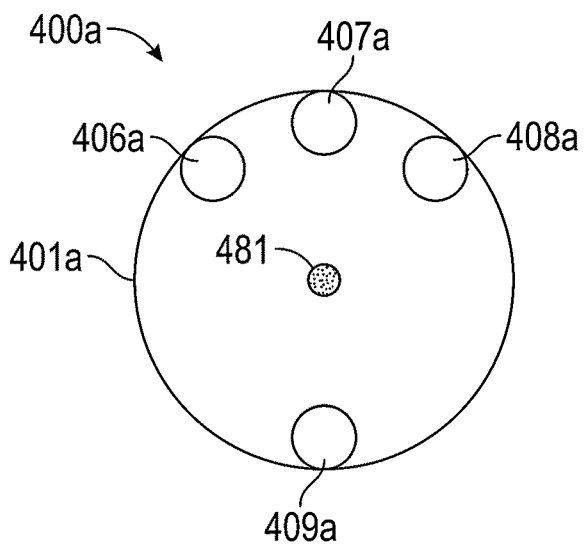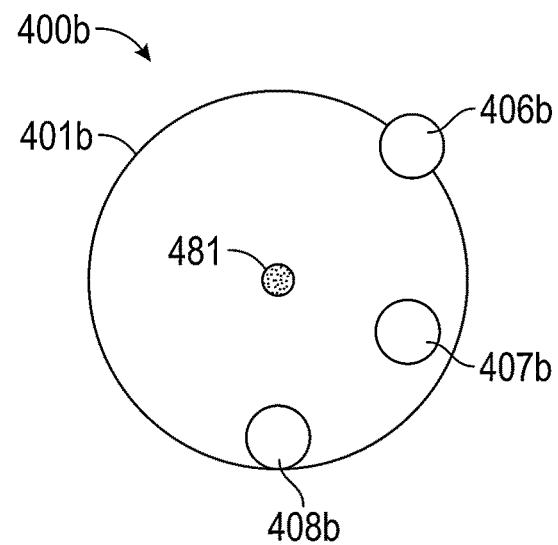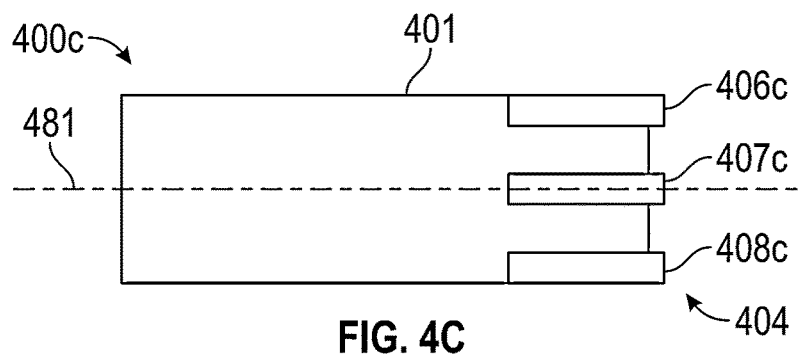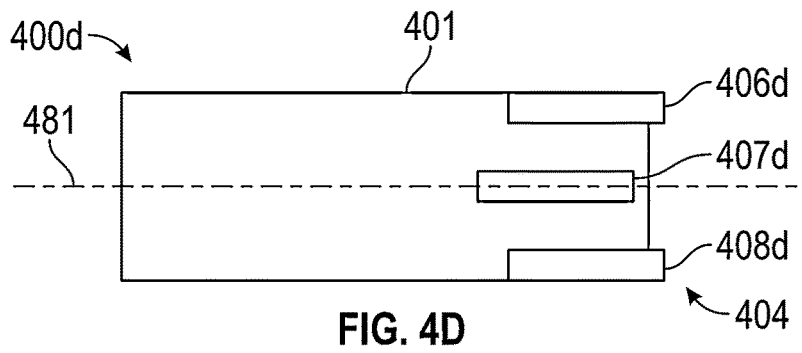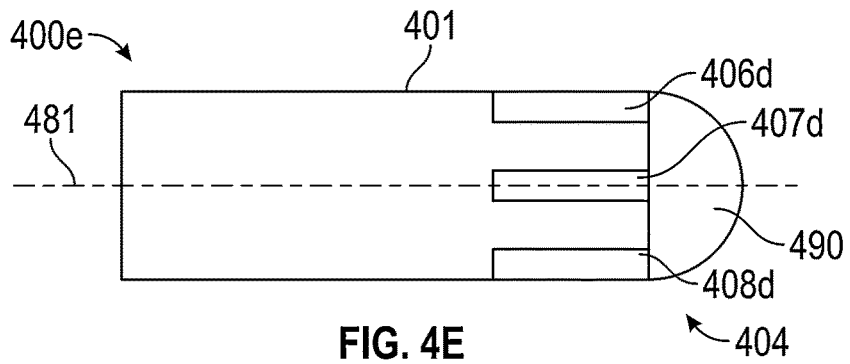

SYSTEMS, DEVICES, AND METHODS FOR GENERATING SHOCK WAVES IN A FORWARD DIRECTION

FIELD

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of 2-4 atm) so that the balloon expands to contact the lesion but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

Calcium buildup in various body structures, such as Mitral Annular Calcification (MAC) and Chronic Total Occlusions (CTOs), can become very thick and thus difficult or even impossible to treat using known methods. As described above, a relatively novel approach for treating such calcification includes introducing a catheter into the affected structure and generating shock waves within the body structure using the catheter to break up the calcifications. Existing shock wave devices typically include shock wave emitters spaced along the length (i.e., along the longitudinal axis) of the device's body and are used to treat buildup of calcified plaque along the length of the inner wall of a body lumen such as a blood vessel. Such devices are not configured for generating shock waves in a forward direction. Shock wave devices configured for forward firing exist, but are not capable of withstanding high voltages, for instance up to 20 kV, and are thus limited in their ability to generate powerful shock waves in the forward direction. Further, known devices include a limited number of forward shock wave emitters (e.g., one or two), which minimizes the constructive interference of the shock waves distally of the end of the device, thus further reducing the capacity of the device to break up dense calcifications.

SUMMARY

Described herein are systems, devices, and methods for generating shock waves that propagate in a substantially forward direction from a distal end of a catheter, for instance, to treat calcified plaques or other calcifications and obstructions in the body that are distal of the distal end of the catheter. In some embodiments, the catheter includes a plurality of shock wave emitters arrayed about a longitudinal axis at the distal end of the catheter. Each of the shock wave emitters includes an electrode pair separated by a spark gap for generating shock waves that propagate forward of the catheter. The forward directed shock waves generated by the shock wave emitters can constructively interfere with one another distally of the distal end of the catheter to produce a powerful peak compressive force for treating dense calcifications, such as Mitral Annular Calcification (MAC) and Chronic Total Occlusions (CTOs).

In some embodiments, the catheters described herein can be inserted into a body lumen such as a blood vessel until the distal end of the catheter is positioned such that a target treatment area in the body lumen is positioned at least partially forward of the distal end of the catheter. Voltage pulses can be applied to a plurality of shock wave emitters located at the distal end of the catheter to generate shock waves directed forward toward the target treatment area. In some embodiments, the shock wave emitters may be encased in an enclosure, such as a cap or balloon that can be filled with a conductive fluid. In some embodiments, the shock wave emitters are not enclosed, and vapor bubbles (e.g., cavitation bubbles) generated by energy discharged from the shock wave emitters can contribute to the treatment of the target area.

According to some aspects, a catheter for use in a body lumen includes a catheter body; and a plurality of shock wave emitters disposed at a distal end of the catheter body, each shock wave emitter configured to generate a shock wave that propagates distally of the catheter body, and wherein at least one shock wave emitter of the plurality of shock wave emitters comprises electrodes separated by a spark gap and at least one electrical connection to an electrode of at least one other shock wave emitter of the plurality of shock wave emitters.

Optionally, the plurality of shock wave emitters are arranged such that shock waves emitted from the plurality of shock wave emitters can constructively interfere distally of the catheter body. Optionally, the plurality of shock wave emitters are electrically connected in series such that an electrical pulse applied across an electrode of a first shock wave emitter of the plurality of shock wave emitters and an electrode at a second shock wave emitter of the plurality of shock wave emitters causes each of the plurality of shock wave emitters to emit a respective shock wave.

Optionally, at least one shock wave emitter of the plurality of shock wave emitters can be driven independently of at least a second shock wave emitter of the plurality of shock wave emitters. Optionally, a first shock wave emitter of the plurality of shock wave emitters comprises an exposed distal tip of a first insulated wire and an exposed distal tip of a second insulated wire, the second insulated wire extending to a second shock wave emitter of the plurality of shock wave emitters.

Optionally, the first insulated wire extends along the length of the catheter body and is positioned within a lumen of the catheter body. Optionally, a first shock wave emitter of the plurality of shock wave emitters comprises an exposed distal end of an insulated wire and a conductive emitter band that is separated from the exposed distal end of the insulated wire by a spark gap.

Optionally, the plurality of shock wave emitters comprises at least three shock wave emitters. Optionally, the plurality of shock wave emitters are arrayed symmetrically about a longitudinal axis of the catheter body. Optionally, a distal most surface of a shock wave emitter of the plurality of shock wave emitters is flush with a distal most surface of the distal end of the catheter body.

Optionally, a distal most surface of a shock wave emitter of the plurality of shock wave emitters is recessed from a distal most surface of the distal end of the catheter body. Optionally, a distal most surface of a shock wave emitter of the plurality of shock wave emitters is positioned forward of a distal most surface of the distal end of the catheter body.

Optionally, the plurality of shock wave emitters are disposed at the same distal location relative to the distal end of the catheter body. Optionally, an outermost surface of a shock wave emitter of the plurality of shock wave emitters is inset relative to an outer circumferential surface of the catheter body. Optionally, an outermost surface of a shock wave emitter of the plurality of shock wave emitters is positioned externally relative an outer circumferential surface of the catheter body.

Optionally, the catheter includes an enclosure positioned to cover the plurality of shock wave emitters at the distal end of the catheter body. Optionally, the enclosure is configured to be filled with a conductive fluid. Optionally, the catheter includes a central lumen extending from the proximal end of the catheter to the distal end of the catheter.

Optionally, the central lumen is configured to receive a guide wire. Optionally, the central lumen is configured to receive a pacemaker wire lead. Optionally, the catheter body comprises an aspiration lumen. Optionally, the plurality of shock wave emitters are respectively spaced apart from one another by a distance of between 1 mm and 10 mm.

According to some aspects, a catheter for use in a body lumen comprises: a catheter body; and at least three shock wave emitters disposed at a distal end of the catheter body, each shock wave emitter configured to generate a shock wave that propagates distally of the catheter body, wherein the at least three shock wave emitters are arrayed about a longitudinal axis of the catheter body such that shock waves emitted from the at least three shock wave emitters can constructively interfere distally of the catheter body, wherein each shock wave emitter comprises electrodes separated by a spark gap. Optionally, the at least three shock wave emitters are all electrically connected in series such that an electrical pulse applied to a first shock wave emitter of the at least three shock wave emitters causes each of the at least three shock wave emitters to emit a respective shock wave. Optionally, at least a first shock wave emitter of the at least three shock wave emitters can be driven independently of at least a second shock wave emitter of the at least three shock wave emitters. Optionally, each shock wave emitter of the at least three shock wave emitters shares a common electrode with each of the other shock wave emitters. Optionally, the common electrode is positioned at an equal distance from an electrode of each of the at least three shock wave emitters.

According to some aspects, a shock wave generating system comprises: a shock wave energy generator; and a catheter comprising: a catheter body; and a plurality of shock wave emitters disposed at a distal end of the catheter body, each shock wave emitter configured to generate a shock wave that propagates distally of the catheter body, wherein the plurality of shock wave sources are arranged such that shock waves emitted from the plurality of shock wave emitters can constructively interfere distally of the catheter body, and wherein each shock wave emitter comprises electrodes separated by a spark gap and at least one electrical connector that connects at least one of the electrodes to an electrode of another shock wave emitter of the plurality of shock wave emitters. Optionally, the shock wave energy generator is configured to deliver high voltage pulses to a shock wave emitter of the plurality of shock wave emitters, wherein the high voltage pulses are between 3 kV and 20 kV, including 3 kV and 20 kV. Optionally, the shock wave energy generator is configured to deliver the voltage pulses at a rate of up to 20 Hz, including 20 Hz. Optionally, the shock wave energy generator applies an alternating current to the electrodes to induce a change in the polarity of the electrodes.

According to some aspects, a method for emitting shock waves in a body lumen comprises: positioning a catheter adjacent to an occlusion in a vessel, the catheter comprising a plurality of shock wave emitters disposed at a distal end of a catheter body; and emitting a first plurality of shock waves from the plurality of shock wave emitters in a distal direction so that the shock waves constructively interfere distally of the distal end of the catheter. Optionally, the method comprises advancing the catheter further into the vessel; and emitting a second plurality of shock waves from the plurality of shock wave emitters so that the shock waves constructively interfere at a location that is distal of the first location. Optionally, the method comprises removing a pacemaker lead from the vessel.

According to some aspects, a catheter for use in a body lumen comprises: a catheter body; and at least three shock wave emitters disposed at a distal end of the catheter body, wherein at least a first shock wave emitter of the at least three shock wave emitters can be driven independently of at least a second shock wave emitter of the at least three shock wave emitters. Optionally, the at least three shock wave emitters are arranged such that shock waves emitted from the at least three shock wave emitters can constructively interfere distally of the catheter body. Optionally, the first shock wave emitter of the at least three shock wave emitters comprises an exposed distal tip of a first insulated wire and an exposed distal tip of a second insulated wire. Optionally, the first insulated wire extends along the length of the catheter body and is positioned within a lumen of the catheter body. Optionally, the first shock wave emitter of the at least three shock wave emitters comprises an exposed distal end of an insulated wire and a conductive emitter band that is separated from the exposed distal end of the insulated wire by a spark gap. Optionally, at least three shock wave emitters are arrayed symmetrically about a longitudinal axis of the catheter body. Optionally, the catheter comprises an enclosure positioned to cover the at least three shock wave emitters at the distal end of the catheter body. Optionally, the enclosure is configured to be filled with a conductive fluid. Optionally, the catheter includes a central lumen extending from the proximal end of the catheter to the distal end of the catheter. Optionally, the central lumen is configured to receive a guide wire Optionally, the central lumen is configured to receive a pacemaker wire lead. Optionally, the catheter body comprises an aspiration lumen. Optionally, the at least three shock wave emitters are respectively spaced apart from one another by a distance of between 1 mm and 10 mm.

According to some aspects, a catheter for use in a body lumen comprises: a catheter body; at least three shock wave emitters disposed at a distal end of the catheter body, each shock wave emitter configured to generate a shock wave that propagates distally of the catheter body; and an enclosure that surrounds the at least three shock wave emitters, wherein shock waves are transmitted through the enclosure. Optionally, at least one shock wave emitter of the at least three shock wave emitters comprises an exposed distal tip of a first insulated wire and an exposed distal tip of a second insulated wire. Optionally, at least one shock wave emitter of the at least three shock wave emitters comprises an exposed distal end of an insulated wire and a conductive emitter band that is separated from the exposed distal end of the insulated wire by a spark gap. Optionally, the enclosure is configured to be filled with a conductive fluid. Optionally, the at least three shock wave emitters are arranged such that shock waves emitted from the at least three shock wave emitters can constructively interfere distally of the catheter body. Optionally, the first shock wave emitter of the at least three shock wave emitters comprises an exposed distal tip of a first insulated wire and an exposed distal tip of a second insulated wire. Optionally, the first shock wave emitter of the at least three shock wave emitters comprises an exposed distal end of an insulated wire and a conductive emitter band that is separated from the exposed distal end of the insulated wire by a spark gap. Optionally, the catheter comprises a central lumen extending from a proximal end of the catheter to the distal end of the catheter. Optionally, the central lumen is configured to receive a guide wire. Optionally, the central lumen is configured to receive a pacemaker wire lead. Optionally, the catheter body comprises an aspiration lumen. Optionally, the at least three shock wave emitters are respectively spaced apart from one another by a distance of between 1 mm and 10 mm.

According to some aspects, a method for removing a pacemaker lead comprises: advancing a catheter along the pacemaker lead to a target site comprising fibrotic tissue, the catheter comprising a plurality of shock wave emitters disposed at a distal end of the catheter body, each shock wave emitter configured to generate a shock wave that propagates distally of the catheter body, and wherein at least one shock wave emitter of the plurality of shock wave emitters comprises electrodes separated by a spark gap and at least one electrical connection to an electrode of at least one other shock wave emitter of the plurality of shock wave emitters; and generating one or more shock waves to at least partially break up the fibrotic tissue so that the pacemaker lead can be removed. Optionally, the target site is within the heart. Optionally, the fibrotic tissue is located distally of the distal end of the catheter. Optionally, the pacemaker lead is inserted into a lumen of the catheter to guide the catheter to the target site. Optionally, the method comprises advancing the catheter further along the pacemaker lead to the target site; and generating one or more additional shock waves. Optionally, the catheter further comprises a plurality of shock wave emitters positioned proximally of the distal end of the catheter body, wherein the second plurality of shock wave emitters are respectively configured to generate shock waves that propagate radially from the catheter body; and wherein the method further comprises: generating a plurality of shock waves that propagate radially of the catheter using the second plurality of shock wave emitters to at least partially break up a calcified region of vasculature leading to the target site.

According to some aspects, a catheter for use in a body lumen comprises: a catheter body comprising a chamber, wherein one or more surfaces that define the chamber are formed of a material that at least partially reflects shock waves; and a plurality of shock wave emitters positioned at least partially within the chamber, wherein each shock wave emitter is configured to generate a shock wave, wherein shock waves generated by the plurality of shock wave emitters are at least partially reflected radially outward from the catheter body through an opening in the chamber. Optionally, each of the plurality of shock wave emitters is positioned adjacent to a surface of the one or more surfaces within the chamber, wherein the surface is configured to reflect shock waves radially outward from the surface. Optionally, at least three surfaces of the chamber are formed of the material that at least partially reflects shock waves. Optionally, the catheter comprises an enclosure positioned to at least partially circumscribe the plurality of shock wave emitters, wherein the enclosure defines an outer diameter of the chamber and is configured to facilitate transmission of shock waves from the chamber to a target treatment site. Optionally, the enclosure is positioned to cover the opening in the chamber. Optionally, the enclosure is configured to be filled with a conductive fluid. Optionally, the shock wave emitters are positioned coplanar with a virtual plane that is perpendicular to a longitudinal axis of the catheter.

According to some aspects, a catheter for use in a body lumen comprises: a catheter body; a first plurality of shock wave emitters disposed at a distal end of the catheter body, each shock wave emitter configured to generate a shock wave that propagates distally of the catheter body; and a second plurality of shock wave emitters positioned proximally of the distal end of the catheter body, wherein the second plurality of shock wave emitters are respectively configured to generate shock waves that propagate radially from the catheter body. Optionally, the catheter comprises an enclosure that surrounds at least the first plurality of shock wave emitters, wherein shock waves generated by the first plurality of shock wave emitters are transmitted through the at least one enclosure. Optionally, the first plurality of shock wave emitters is configured to generate a first plurality of shock waves independently of the second plurality of shock wave emitters. Optionally, the first plurality of shock wave emitters is configured to generate a plurality of shock waves simultaneously with the second plurality of shock wave emitters. Optionally, the second plurality of shock wave emitters are positioned at least partially within a chamber of the catheter body, wherein each shock wave emitter of the second plurality of shock wave emitters is configured to generate a shock wave, wherein shock waves generated by the plurality of shock wave emitters are at least partially reflected radially outward from the catheter body through an opening in the chamber. Optionally, one or more surfaces that define the chamber are formed of a material that at least partially reflects shock waves. Optionally, the catheter comprises an enclosure positioned to at least partially circumscribe the second plurality of shock wave emitters, wherein the enclosure defines an outer diameter of the chamber and is configured to facilitate transmission of shock waves from the chamber to a target treatment site. Optionally, at least a first shock wave emitter of the first plurality of shock wave emitters can be driven independently of at least a second shock wave emitter of the first plurality of shock wave emitters. Optionally, at least a first shock wave emitter of the second plurality of shock wave emitters can be driven independently of at least a second shock wave emitter of the second plurality of shock wave emitters. Optionally, at least one shock wave emitter of the first plurality of shock wave emitters can be driven independently of at least one shock wave emitter of the second plurality of shock wave emitters. Optionally, the first plurality of shock wave emitters comprises at least three shock wave emitters. Optionally, the second plurality of shock wave emitters comprises at least three shock wave emitters. Optionally, the first plurality of shock wave emitters and the second plurality of shock wave emitters both comprise at least three shock wave emitters.

BRIEF DESCRIPTION OF THE FIGURES

The invention will now be described, by way of example only, with reference to the accompanying drawings, in which:

FIG. 4A illustrates a front view of a catheter including a plurality of shock wave emitters, according to some embodiments.

FIG. 4B illustrates a front view of a catheter including a plurality of shock wave emitters, according to some embodiments.

FIG. 4C illustrates a side view of a catheter including a plurality of shock wave emitters, according to some embodiments.

FIG. 4D illustrates a side view of a catheter including a plurality of shock wave emitters, according to some embodiments.

FIG. 4E illustrates a side view of a catheter including a plurality of shock wave emitters encased in an enclosure, according to some embodiments.

DETAILED DESCRIPTION

Figure 1A:
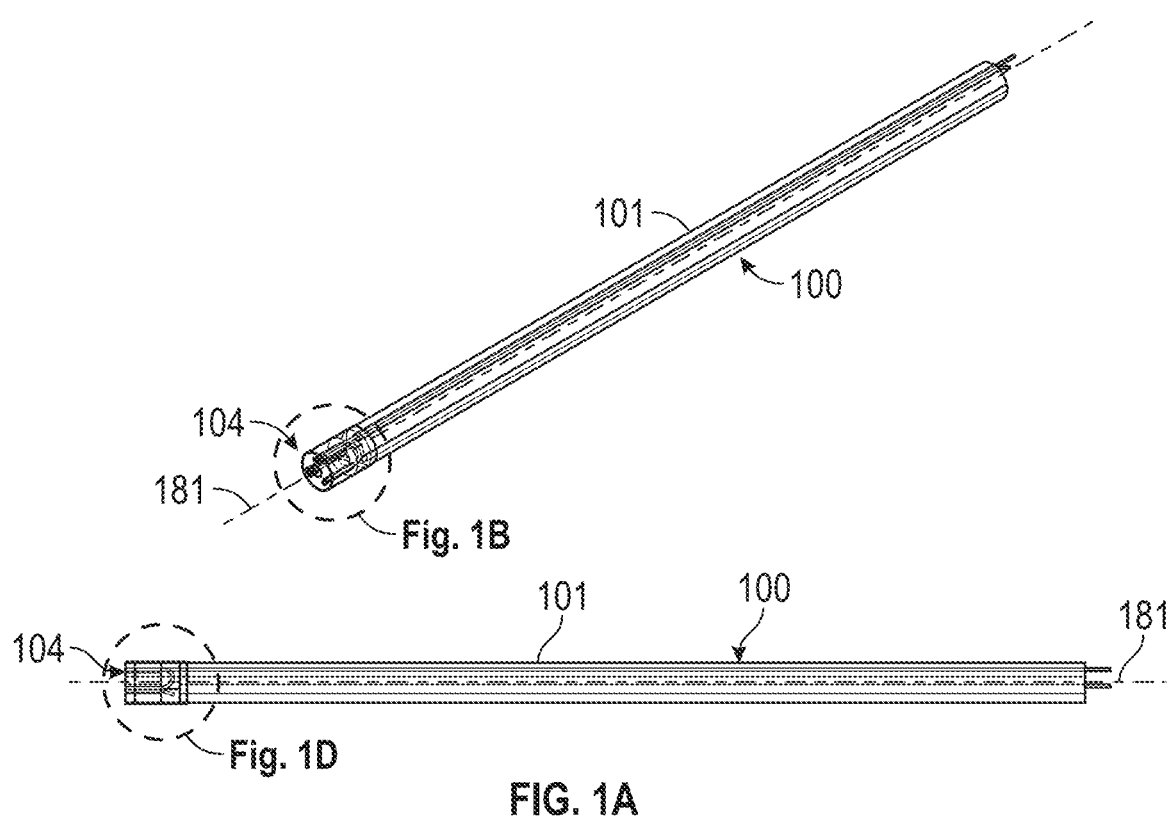
FIG. 1A illustrates an isometric view and a side view of a catheter including a plurality of shock wave emitters, according to some embodiments.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, 9,433,428, and 10,709,462, and in U.S. Publication No. 2021/0085383 all of which are incorporated herein by reference. Other catheter designs have improved the delivery of shock waves, for instance, by specific electrode construction and configuration thereby directing shock waves in a forward direction to break up tighter and harder-to-cross occlusions in vasculature. Examples of forward-firing catheter designs can be found in U.S. Pat. Nos. 10,966,737, 11,478,261, and 11,596,423 and U.S. Publication Nos. 2023/0107690 and 2023/0165598, all of which are incorporated herein by reference.

Described herein are devices, systems, and methods for generating shock waves that propagate in a substantially forward direction, which can be used to treat vascular diseases, such as Chronic Total Occlusion (CTO), Mitral Annular Calcification (MAC), or circumferential calcium, or to treat urinary diseases, such as concretions or kidney stones in the ureter. In accordance with the present disclosure, a catheter includes a catheter body and a plurality of shock wave emitters positioned at a distal end of the catheter body. In some embodiments, each shock wave emitter includes at least two electrodes separated by a spark gap. The electrodes are positioned such that when a high voltage is applied across the electrodes, a shock wave is generated that propagates in a direction forward of the distal end of the catheter body. Shock waves generated by the multiple emitters may constructively interfere forward of the distal end of the catheter body, amplifying the compressive force of the shock waves for treating calcifications forward of the catheter body.

In some embodiments, a plurality of emitters are disposed at the distal end of the catheter. An emitter may include a pair of electrodes that are formed by the exposed distal ends of two wires. In some embodiments, one of the two wires of a first emitter extends to a second emitter to form an electrode of the second emitter. A third wire may have an exposed distal end at the second emitter that forms an electrode pair with the exposed distal end of the wire extending from the first emitter. The third wire may also extend to a third emitter to form part of an electrode pair at the third emitter, and so on for additional emitters. The wires extending between each of the respective emitters may be routed through lumens in the catheter body extending from one emitter to the next.

In some embodiments, an emitter includes a first electrode formed by an exposed conductive end of a wire and a second electrode formed by a conductive band surrounding the end of the wire. The end of the wire is spaced from the conductive band by a spark gap. A third electrode formed by an end of a second wire may be connected to both the first conductive band and a second conductive band to transfer electrical current between the two bands. The second conductive band may form part of an electrode pair with an end of a third wire, thus forming the next emitter in a series of emitters. Any number of emitters may be connected in series by extending wires between conductive bands to transfer an electrical current between each respective band.

In some embodiments, a wire of one of the electrodes at an emitter extends along the catheter body toward a negative terminal of a voltage source, and a wire of an electrode at a different emitter extends along the catheter body toward a positive terminal of the voltage source. Accordingly, plurality of shock wave emitters may be connected in series to a voltage generator via the two wires such that when voltage pulses are applied across the wires at the negative and positive terminal, shock waves are emitted from each of the respective shock wave emitters.

In any of the emitter configurations described herein, voltage polarity (i.e., direction of current flow) may be switched between voltage pulses. Such polarity switching may promote more uniform wear of electrodes and extend device longevity.

In some embodiments, at least one of the shock wave emitters can be driven independently of at least one other shock wave emitter. For instance, one or more emitters may include an electrode pair formed from the exposed tips of two wires, and each of the wires may extend along the length of the catheter body to connect to a respective negative and positive terminal at a voltage source. Additionally, or alternatively, one or more emitters may include an electrode pair formed from an exposed end of a first insulated wire separated by a spark gap from a conductive band. An exposed end of a second insulated wire may be connected to the emitter band, and both the first and second insulated wires may extend along the length of the catheter body to connect to a respective negative and positive terminal at a voltage source. When a voltage is applied across the two wires connected to the voltage source, a shock wave can be generated at the respective shock wave emitter without producing shock waves at any other emitters provided on the catheter. Accordingly, in some instances, the design is such that each electrode pair can spark separately from the other electrode pairs, including adjacent electrode pairs. The emitters may be driven sequentially, for instance, in a clockwise and or counter-clockwise manner.

In some embodiments, the shock wave emitters are enclosed within an enclosure such as a fluid filled cap or balloon. The cap or balloon may mitigate thermal injury to soft tissue and reduce cavitation stresses by limiting expansion of the vapor bubbles produced during shock wave generation to the interior of the cap. For instance, the vapor bubbles hit the enclosure wall before reaching their maximum potential size, thus inducing collapse, and reducing cavitation stress and preventing soft tissue injury that can be caused by tensile stresses during cavitation bubble collapse. As described further below, the shape of the enclosure may also impact the form of the shock waves and vapor bubbles as well as the manner in which these shock waves and vapor bubbles propagate forward of the catheter. In some embodiments, the shock wave emitters are exposed at the distal end of the catheter and cavitation bubble formation and collapse on the surface of the target calcification further contributes to fragmentation of the calcification.

Shock wave emitters may be connected to a voltage pulse generator capable of applying high voltage, high frequency electrical pulses to simultaneously generate a plurality of shock waves from the plurality of shock wave emitters that can propagate forward of the distal end of the catheter to impinge on a treatment area positioned distal of the catheter. In some embodiments, the catheters described herein may be connected to a pump in communication with a fluid source for injecting a conductive fluid such as saline and/or contrast solution into the catheter. In some embodiments, the conductive fluid is injected into an enclosure that encloses the plurality of shock wave emitters, as described above.

In some embodiments, the catheters described herein can be inserted into a body lumen, such as a blood vessel, for instance, to treat a buildup of calcification. The catheter may be advanced within the body lumen until the distal end of the catheter reaches a desired distance from the target treatment area. Once in position, a plurality of shock waves may be emitted from the plurality of shock wave emitters such that the shock waves propagate in a unison direction toward the target treatment area. In some embodiments, the shock waves constructively interfere with one another distally of the distal end of the catheter, thus compounding the peak compressive force of the plurality of shock waves relative to each of the individual shock waves emitted by the respective shock wave emitters. In some embodiments, after breaking up a portion of the target treatment area (e.g., a portion of the calcification/occlusion), the catheter may be advanced further into the vessel toward a second target treatment area (e.g., a newly exposed portion of the occlusion/calcification), and a second plurality of shock waves may be emitted targeting the treatment area. This process may be iterated any number of times until the occlusion/calcification has been successfully treated.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The terms "emitter sheath" and "emitter band" refers to a continuous or discontinuous band of conductive material that may form one or more electrodes of one or more electrode pairs, thereby forming a location of one or more emitters.

In some embodiments, the catheters described herein may be an IVL catheter. In some embodiments, an IVL catheter may be a so-called "rapid exchange-type" ("Rx") catheter provided with an opening portion through which a guide wire can be guided (e.g., through a middle portion of a central tube in a longitudinal direction). In other embodiments, an IVL catheter may be an "over-the-wire-type" ("OTW") catheter in which a guide wire lumen is formed throughout the overall length of the catheter, and a guide wire is guided through the proximal end of a hub.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and cavitation bubbles.

In the following description of the disclosure and embodiments, reference is made to the accompanying drawings in which are shown, by way of illustration, specific embodiments that can be practiced. It is to be understood that other embodiments and examples can be practiced and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

FIGS. 1A-1D illustrate an exemplary catheter 100 for generating shock waves in a forward direction, according to some embodiments. The catheter 100 may be used to fragment, crack, or otherwise break up calculi within the human body, for instance, to treat various occlusions within blood vessels, kidney stones in the ureter, and so on.

FIG. 1A illustrates an isometric view and a side view of a distal portion of a catheter 100. The catheter 100 of FIG. 1A includes a catheter body 101 with a distal end 104. A plurality of shock wave emitters 106, 108, and 110 (shown more clearly in FIG. 1B) are positioned at the distal end 104 of the catheter body 101. Each shock wave emitter 106-110 is configured to generate a shock wave that propagates distally of the catheter body 101 (i.e., distally of distal end 104). In some embodiments, the catheter body 101 may have an outer diameter of between 3 Fr and 14 Fr (French Gauge). In some embodiments, the catheter body 101 may have an outer diameter of between 1 Fr and 20 Fr. In some embodiments, the catheter body 101 may have an outer diameter of between 1 Fr and 100 Fr. In some embodiments, the catheter body 101 may have an outer diameter of at least 1 Fr, at least 2 Fr, at least 3 Fr, at least 4 Fr, at least 5 Fr, at least 6 Fr, at least 7 Fr at least 8 Fr, at least 9 Fr, at least 10 Fr, at least 11 Fr, at least 12 Fr, at least 13 Fr, at least 14 Fr, at least 15 Fr, at least 16 Fr, at least 17 Fr, at least 18 Fr, at least 19 Fr, or at least 20 Fr. In some embodiments, the catheter body may have an outer diameter of no more than 20 Fr, no more than 19 Fr, no more than 18 Fr, no more than 17 Fr, no more than 16 Fr, no more than 15 Fr, no more than 14 Fr, no more than 13 Fr, no more than 12 Fr, no more than 11 Fr, no more than 10 Fr, no more than 9 Fr, no more than 8 Fr, no more than 7 Fr, no more than 6 Fr, no more than 5 Fr, no more than 4 Fr, no more than 3 Fr, no more than 2 Fr, or no more than 1 Fr.

Figure 11A:
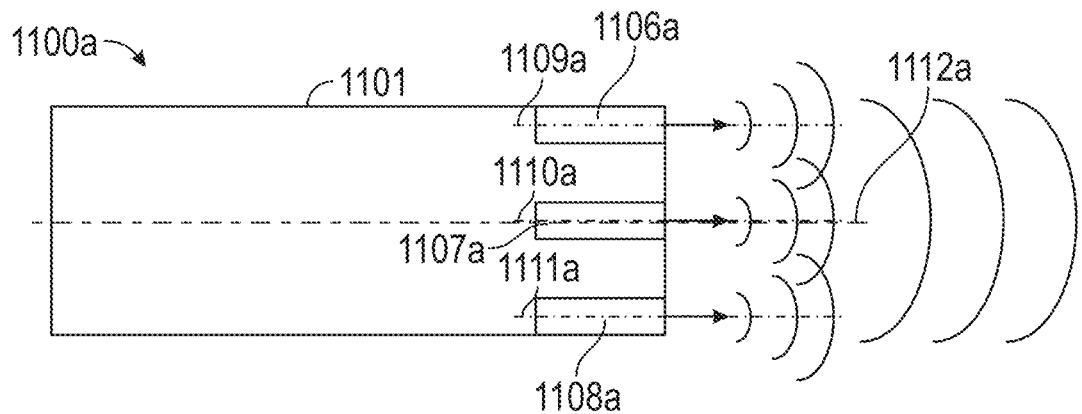
FIGS. 11A-11C illustrate directional control and constructive interference of shock waves using different shock wave emitter and catheter body configurations.
Figure 11B:
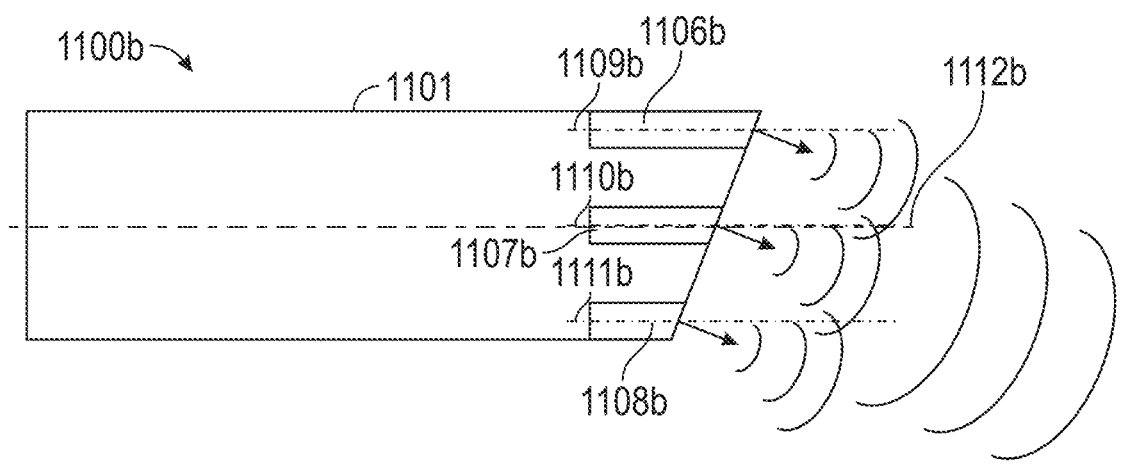
Figure 11C:
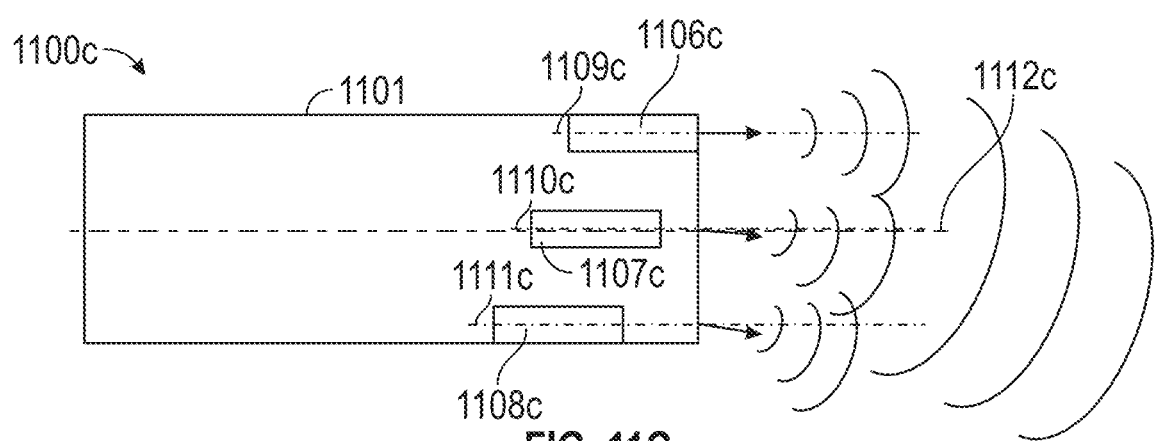

When a sufficiently high voltage (pulse) is applied across two electrodes at each shock wave emitter, a shock wave is generated at each shock wave emitter as electrical current flows from the first electrode to the second electrode, resulting in a plurality of shock waves from the plurality of shock wave emitters. The shock wave emitters 106-110 may be arranged such that shock waves emitted from the plurality of shock wave emitters 106-110 to constructively interfere distally of the catheter body 101. Thus, the positioning of the shock wave emitters 106-110 can maximize the shock wave intensity distally of the catheter body by causing shock waves emitted by each respective emitter to combine with one another to produce an amplified combined shock wave, for instance as illustrated in FIGS. 11A-11C.

Figure 1B:
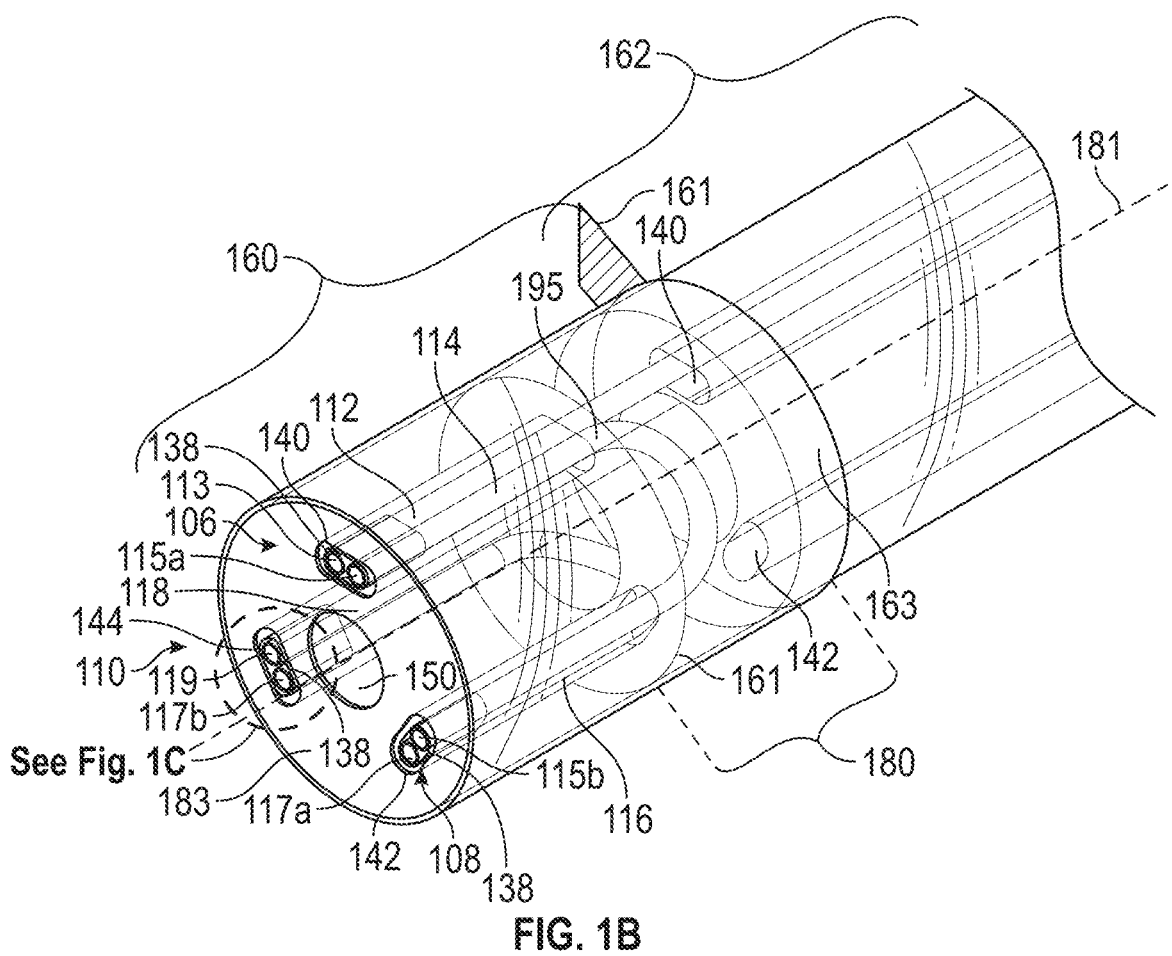
FIG. 1B illustrates a detailed isometric view of a distal end of the catheter of FIG. 1A, according to some embodiments.

FIG. 1B illustrates a detailed isometric view of the distal end 104 of catheter 100. In the illustrated embodiment, the shock wave emitters 106, 108, and 110 are evenly spaced (positioned at increments of about 120 degrees) about the longitudinal axis 181; however, as described throughout the specification, a variety of different spacing configurations can be implemented without deviating from the scope of the disclosure. In some embodiments, the shock wave emitters may be spaced apart from one another by a distance of between 0.1 mm and 20 mm. In some embodiments, the shock wave emitters may be spaced apart from one another by a distance of between 1 mm and 10 mm. In some embodiments, the shock wave emitters may be spaced apart from one another by between 2 mm and 5 mm. The shock wave emitters may be spaced apart from one another by at least 1 mm, at least 2 mm, at least 3 mm, at least 4 mm, at least 5 mm, at least 6 mm, at least 7 mm, at least 8 mm, at least 9 mm, at least 10 mm, at least 12 mm, at least 13 mm, at least 14 mm, at least 15 mm, at least 16 mm, at least 17 mm, at least 18 mm, at least 19 mm, or at least 20 mm. The shock wave emitters may be spaced apart from one another by no more than 20 mm, no more than 19 mm, no more than 18 mm, no more than 17 mm, no more than 16 mm, no more than 15 mm, no more than 14 mm, no more than 13 mm, no more than 12 mm, no more than 11 mm, no more than 10 mm, no more than 9 mm, no more than 8 mm, no more than 7 mm, no more than 6 mm, no more than 5 mm, no more than 4 mm, no more than 3 mm, no more than 2 mm, or no more than 1 mm. The emitters may be spaced apart from one another by a distance set to optimize the constructive interference of shock waves generated by the emitters (e.g., depending on sonic output from individual emitters, acoustic properties of the propagating medium, etc.) In some embodiments, the distance between shock wave emitters is the distance between the two center points of two respective electrode pairs. In some embodiments, the distance between shock wave emitters is measured as the distance between the center points of two respective emitter bands.

In the exemplary embodiment of FIG. 1B, a first shock wave emitter 106 of the plurality of shock wave emitters includes a distal tip 113 of a first insulated wire 112. The insulated wire 112 extends along the length of the catheter body 101 from the distal end 104 (e.g., so that it can be connected to a voltage source proximally of the distal end (for instance, at a proximal end of the catheter), as described further below). A second insulated wire 114 extends from the first shock wave emitter 106 to the second shock wave emitter 108. The second insulated wire includes a first exposed distal tip 115a forming an electrode pair with distal tip 113 separated by a spark gap, thus forming shock wave emitter 106, and a second exposed distal tip 115b forming part of an electrode pair at shock wave emitter 108, as described below. As used herein, an "exposed end," "exposed tip," and/or "exposed distal tip" of an insulated wire may refer to a portion of the wire from which the insulation has been removed, thus revealing a portion of the conductive wire. However, while the emitters herein are often described as including the exposed distal ends/tips of insulated wires, it should be understood that any suitable conductor may serve as an electrode of the emitters.

The second insulated wire 114 extends proximally from shock wave emitter 106 into the catheter body 101 for a first distance, and loops around, for instance as illustrated by the bend 195 forming the U-shaped portion of insulated wire 114, to extend distally toward shock wave emitter 108. A third insulated wire 116 includes a first exposed distal tip 117a at shock wave emitter 108. The second exposed distal tip 115b of second insulated wire 114 and first exposed distal tip 117b of the third insulated wire 116 form an electrode pair separated by a spark gap, thus forming shock wave emitter 108. The third insulated wire 116 wire extends from the second shock wave emitter 108 to a third shock wave emitter 110. Similar to the second insulated wire 114, the third insulated wire 116 extends proximally into the catheter body 101 for a first distance, and loops around to extend distally toward shock wave emitter 110. The third insulated wire 116 includes a second exposed distal tip 117b at shock wave emitter 110, forming an electrode pair with exposed distal tip 119 of a fourth insulated wire. The exposed distal tips 117b and 119 form an electrode pair separated by a spark gap, thus forming third shock wave emitter 110. The fourth insulated wire 118 extends proximally into the catheter body and along the length of the catheter body 101 from the distal end 104 to connect to a positive terminal of a voltage source. Accordingly, when a voltage is applied across the first insulated wire 112 connected to the negative terminal of the voltage source and the fourth insulated wire connected to the positive terminal of the voltage source, a plurality of shock waves are simultaneously generated as an electrical current traverses the spark gaps separating the exposed distal tips of each insulated wire at shock wave emitters 106-110.

In some embodiments, the shock wave emitters 106-110 of the catheter 100 shown in FIG. 1B are electrically connected in series such that an electrical pulse applied across insulated wires connected to a negative and positive terminal of a voltage source (such as wire 112 and 118), respectively, causes each of the plurality of shock wave emitters to emit a respective shock wave. In some embodiments, at least one first shock wave emitter of a plurality of shock wave emitters can be driven independently of at least a second shock wave emitter of the plurality of shock wave emitters. Accordingly, in some embodiments, rather than extending wires between all of the shock wave emitters such that applying a single voltage pulse causes each of the shock wave emitters to generate shock waves in series, one or more shock wave emitters can each include an electrode pair configured to generate shock waves independently of the other shock wave emitters. In some embodiments, the electrode pair at each shock wave emitter (e.g., shock wave emitters 106-110) can be formed of the exposed distal tips of a first and second wire that each extend along the length of catheter 100 from the distal end 104 to electrically couple to a respective positive and negative terminal (or to ground) of a voltage source (i.e., each shock wave emitter may be connected to a respective channel of a relay such that it can be driven independently of the other emitters). In such embodiments, when a voltage pulse is applied across the first and second wire of an independently driven shock wave emitter, a current flows from an exposed distal tip of the first insulated wire to the exposed distal tip of the second insulted wire to generate a shock wave, but that shock wave emitter is electrically isolated from the remaining shock wave emitters.

In some embodiments, catheter body 101 includes one or more lumens extending within the catheter body. In some embodiments, one or more of the insulated wires (e.g., wires 112 and 118 in FIG. 1B) extend along the length of the catheter within a respective lumen to connect to a voltage source. As described above, other insulated wires (e.g., wires 114 and 116 of FIG. 1B) are routed between respective shock wave emitters to carry the current received from the voltage between each of the emitters. Accordingly, the wires routed between respective shock wave emitters may extend into a first lumen of the catheter body 101 in a first direction toward a first shock wave emitter and extend into a second lumen in a second direction toward a second shock wave emitter. As depicted in FIG. 1B, insulated wire 114 is formed into a U-shape, where the parallel portions of the U-shape respectively of extend into lumens 140 and 142. The bend 195 in the U-shape of wire 114 is formed within a cavity 180 formed between a surface 161 of a first section 160 of catheter body 101 and second surface 163 of a second section 162 of the catheter body 101 near the distal end 104. In some embodiments, lumens 140, 142, and/or 144 extend from respective orifices in the distal most surface of catheter 100 at distal end 104 into section 160 of the catheter body 101 to a respective orifice of surface 161 facing cavity 180. In some embodiments, any of the respective lumens 140, 142, and/or 144 extend into the second section 162 of catheter body 101 from a respective orifice of surface 163 on the opposite side of cavity 180 along the same respective longitudinal axes as in section 162.

In some embodiments, cavity 180 is formed into section 160 of catheter body 101. Section 160 may be a removable tip that can be friction fit onto section 162. Cavity 180 may be a hollow portion of section 160 that is configured such that a portion 161 of section 162 can extend into the cavity 180 when section 160 is friction fit with section 162 (e.g., such that sections 160 and 162 overlap with one another when section 160 is friction fit to section 162). The removability of section 160 from section 162 can allow for placement/replacement of wires and/or other device maintenance.

In some embodiments, the catheter 100 includes a central lumen 150 extending from the distal end 104 of the catheter along the length of the catheter body 101. In some embodiments the central lumen 150 may be enclosed within a tube 152 that extends from section 160 to section 162 through cavity 180 within the catheter body 101, as shown in FIG. 1D. In some embodiments, the central lumen 150 extends from an orifice at the distal end 104 to an orifice at the opposite end of catheter body 101. The central lumen 150 may be configured to receive a guide wire. For instance, the guide wire can be inserted into the catheter 100 via central lumen 150 proximally of the distal end 104 and exit the catheter via the central lumen 150 at the distal end 104. The guide wire can be used to guide the catheter into place within a body lumen (e.g., blood vessel, urinary tract, or other organ).

Figure 9:
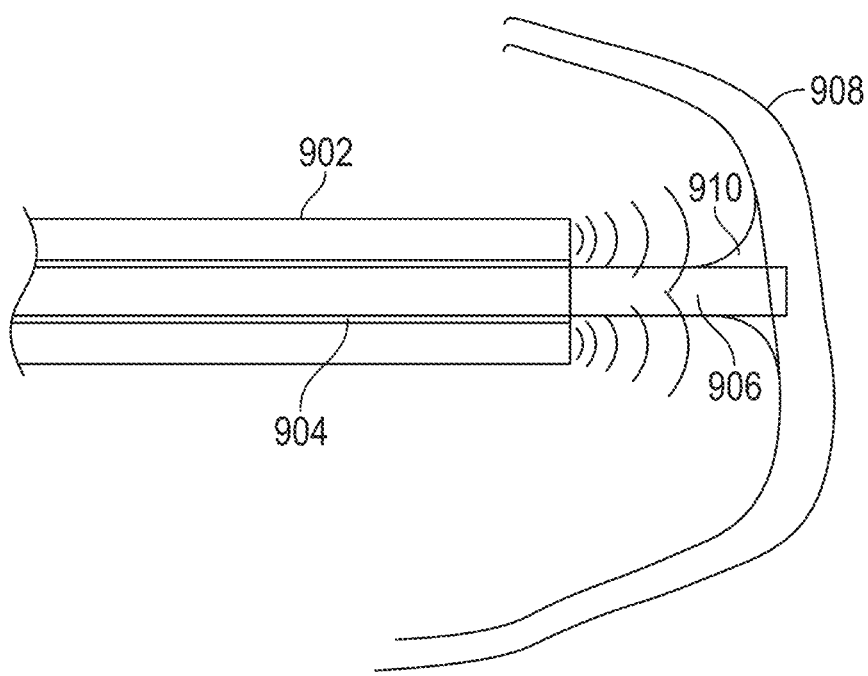
FIG. 9 illustrate an exemplary catheter including a plurality of shock wave emitters and a lumen for removing a pacemaker lead.

In some embodiments, the central lumen 150 is configured to receive a pacemaker wire lead at the distal end 104 of the catheter body 101 for removing the pacemaker wire lead from a tissue, such as cardiac tissue (for instance, as shown in FIG. 9). Pacemaker leads can be difficult to remove due to dense calcification and/or fibrotic tissue build-up. This calcification build-up can make extraction more difficult for the physician and riskier for the patient. The catheter described herein can be used to first break-up these dense calcifications using the shock waves generated by the plurality of shock wave emitters before removing the pacemaker lead. Breaking up the calcifications prior to removing the leads can lead to dramatic reduction in removal time.

In some embodiments, the catheter body 101 includes an aspiration lumen. In some embodiments, the aspiration lumen is for removing debris from a body lumen. In some embodiments central lumen 150 can be configured for aspiration. In some embodiments, the catheter body may include a separate lumen in addition to the central lumen 150 for aspiration. In some embodiments, the catheter 100 includes a marker band for determining an orientation of the catheter within a body lumen.

Figure 1C:
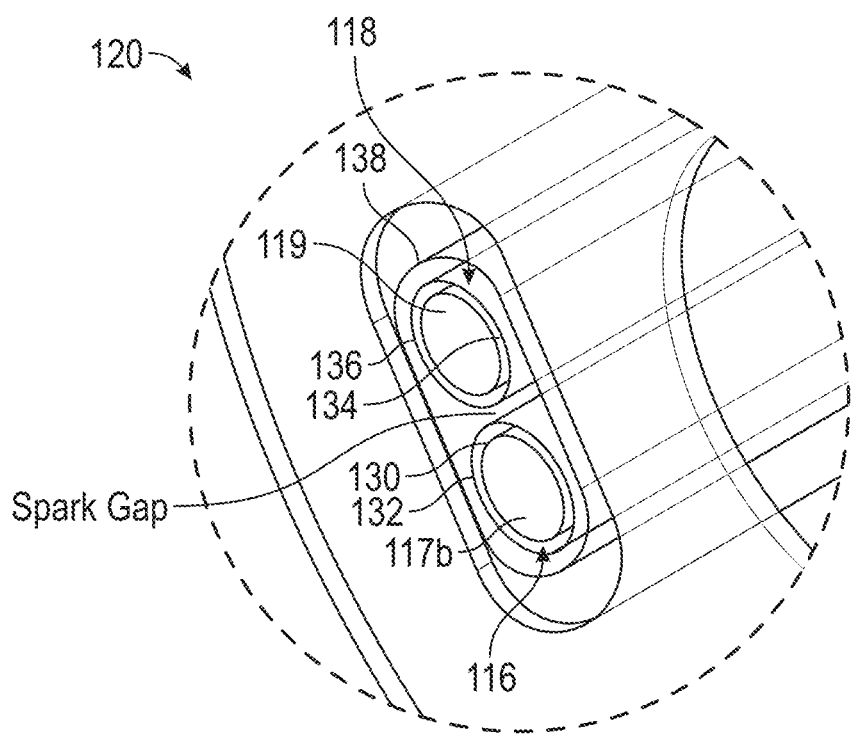
FIG. 1C illustrates a detailed isometric view of a shock wave emitter of the catheter of FIG. 1A, according to some embodiments.
Figure 1D:
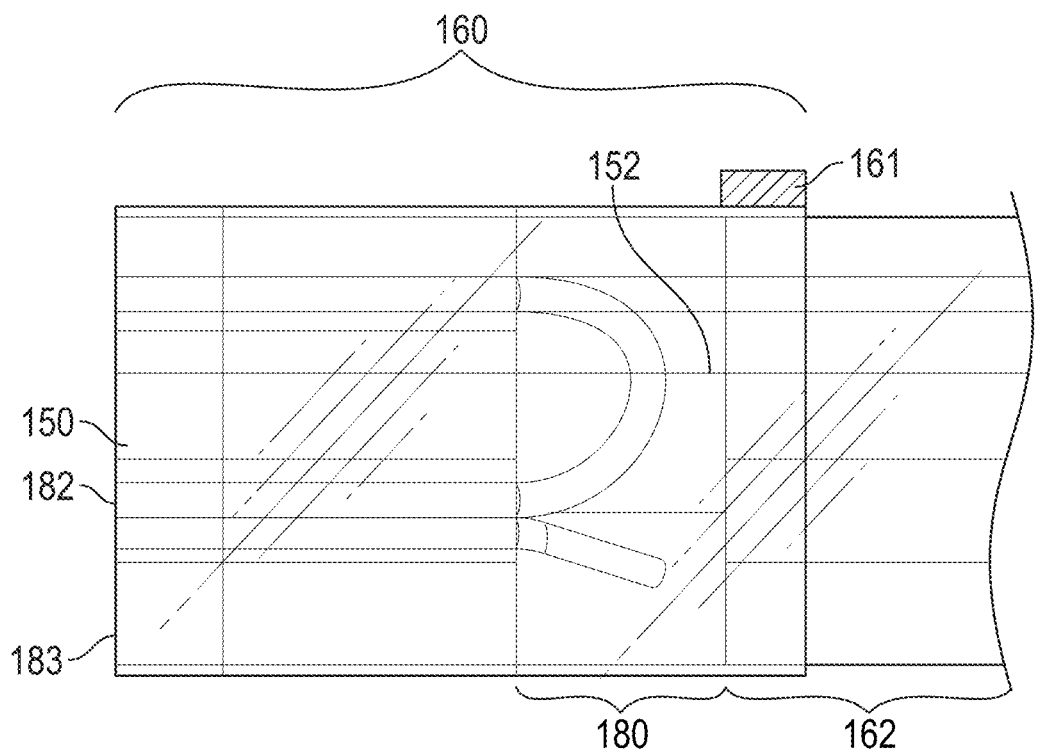
FIG. 1D illustrates a detailed side view of a distal end of the catheter of FIG. 1A, according to some embodiments.

FIG. 1C illustrates a detail view of shock wave emitter 110, in accordance with some embodiments. Shock wave emitter 110 includes insulated wire 116 and insulated wire 118 described above with reference to FIG. 1B. Insulated wire 116 includes a conductive wire 130 disposed within an insulating tube 132. In some embodiments, the conductive wire 130 is a copper wire and insulating tube 132 is a polyimide tube. Similarly, insulated wire 118 includes a conductive wire 134 disposed within an insulating tube 136. In some embodiments, the conductive wire 134 is a Molybdenum wire and the insulating tube 136 is also a polyimide tube. In some embodiments, at least a portion of both of the insulating tubes 132 and 136 are disposed within a single outer insulating tube 138. In some embodiments, the outer insulating tube 138 is also a polyimide tube that provides an additional layer of insulation. The outer insulating tube 138 may separate the two insulated wires 116 and 118 from one another (e.g., by surrounding a portion of each of the insulated wires individually), and in turn separate their respective exposed distal tips (117b and 119) by a spark gap. An outer insulating tube 138 may be positioned at each of shock wave emitters 106, 108, and 110 to provide an additional layer of insulation and to maintain a spark gap between the exposed distal tips (e.g., 117a, 115b, 115a, and 113). As described above, the distal tips 117b and 119 of conductive wires 130 and 134, respectively, are exposed at the distal end of the catheter 100 to allow for generation of shock waves. The exposed distal tips 117b and 119 form an electrode pair separated by a spark gap such that when a voltage is applied across the conductive wires 130 and 134, a current flows from exposed distal tip 117b to the exposed distal tip 119 to generate a shock wave.

In some embodiments, the shock wave emitters 106-110 are arrayed symmetrically about the longitudinal axis 181 of the catheter body, for instance, as shown in FIG. 1B. In some embodiments, the shock wave emitters are instead arrayed asymmetrically about the longitudinal axis of the catheter body. For example, two of the shock wave emitters may be positioned more closely to one another than a third shock wave emitter. Symmetric arrangement of the shock wave emitters about the longitudinal axis may be desirable for optimizing constructive interference between all of the shock wave emitters. However, arranging the shock wave emitters asymmetrically about the axis can provide for asymmetric shock waves, which may be beneficial, for instance, if an occlusion is concentrated at various locations within a body lumen relative to the distal end 104 of the catheter 100 (i.e., if the occlusion is more concentrated at various location about the circumference of the catheter 100).

In some embodiments, a distal most surface 182 of one or more shock wave emitters of the plurality of shock wave emitters is flush with a distal most surface 183 of the distal end of the catheter body, for instance, as shown in FIG. 1D. In some embodiments, a distal most surface 182 of a shock wave emitter of the plurality of shock wave emitters is instead positioned forward from a distal most surface 183 of the distal end of the catheter body 101, for instance, as shown in FIG. 4D. Such a configuration may be preferable, for instance, if direct contact between the shock wave emitters and an occlusion is desired. Alternatively, the distal most surface of any of the shock wave emitters may be recessed from a distal most surface of the distal end of the catheter body, also as shown in FIG. 4D. Such a design be preferred over the flush configuration if a user desired to prevent direct contact between the shock wave emitters and the occlusion/calcification. Additionally, when the distal most surfaces of the shock wave emitters are recessed from the distal most surface of the distal end of the catheter body, the resulting cavitation after pulsing the shock wave emitters may travel further distally of the catheter body relative to when the distal most end of the emitters is positioned flush with the distal most end of the catheter body and/or may produce a greater sonic output relative to when the distal most end of the emitters is positioned flush with the distal most end of the catheter body.

In some embodiments, the plurality of shock wave emitters (e.g., 106-110) are arrayed about a longitudinal axis of the catheter body at the same distal location relative to the distal end of the catheter body, for instance, as shown in FIG. 1D. In some embodiments, a first shock wave emitter of the plurality of shock wave emitters is positioned at a first location relative to the distal end of the catheter body and a second shock wave emitter of the plurality of shock wave emitters is positioned at a second location relative to the distal end of the catheter body. For example, a first shock wave emitter may be positioned such that its distal most surface is flush with the distal end 104 of the catheter body 101, one or more of the shock wave emitters may be positioned distally relative to the first shock wave emitter, and one or more shock wave emitters may be placed proximally relative to the first shock wave emitter. Alternatively, a first shock wave emitter may be positioned such that its distal most surface is flush with the distal end 104 of the catheter body 101, a second shock wave emitter may be positioned proximally relative to the first shock wave emitter, and a third shock wave emitter may be positioned proximally relative to the second shock wave emitter. It should be understood that the aforementioned configurations are meant to be exemplary, and the shock wave emitters could be positioned in a variety of different locations relative to one another without deviating from the scope of this disclosure. A variety of different arrangements of the shock wave emitters that may be included on catheter 100 are shown below in FIGS. 4A-4E. Additionally, it should be understood that while catheter 100 is described as including three shock wave emitters, in some embodiments, the catheters described herein may include additional shock wave emitters (i.e., more than the three provided on catheter 100) positioned at the distal end of the catheter body. The additional shock wave emitters may be included, for instance, to generate a more powerful shock wave for treating occlusions or otherwise breaking up calculi within a human body.

Figure 2A:
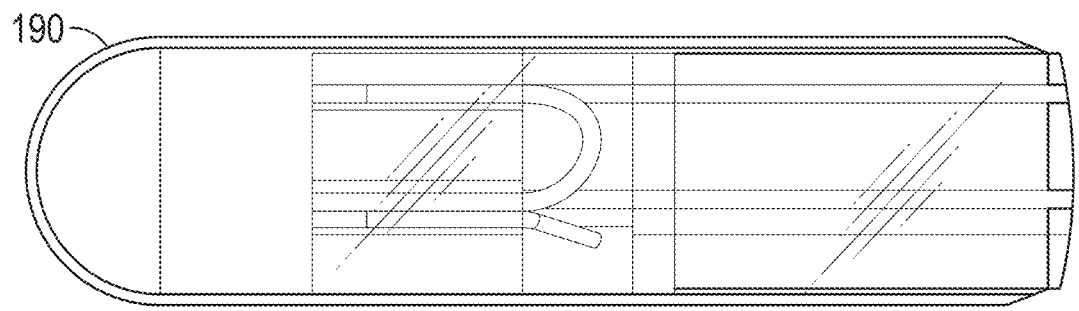
FIG. 2A illustrates a side view of a distal end of a catheter including a plurality of shock wave emitters encased in an enclosure, according to some embodiments.
Figure 2B:
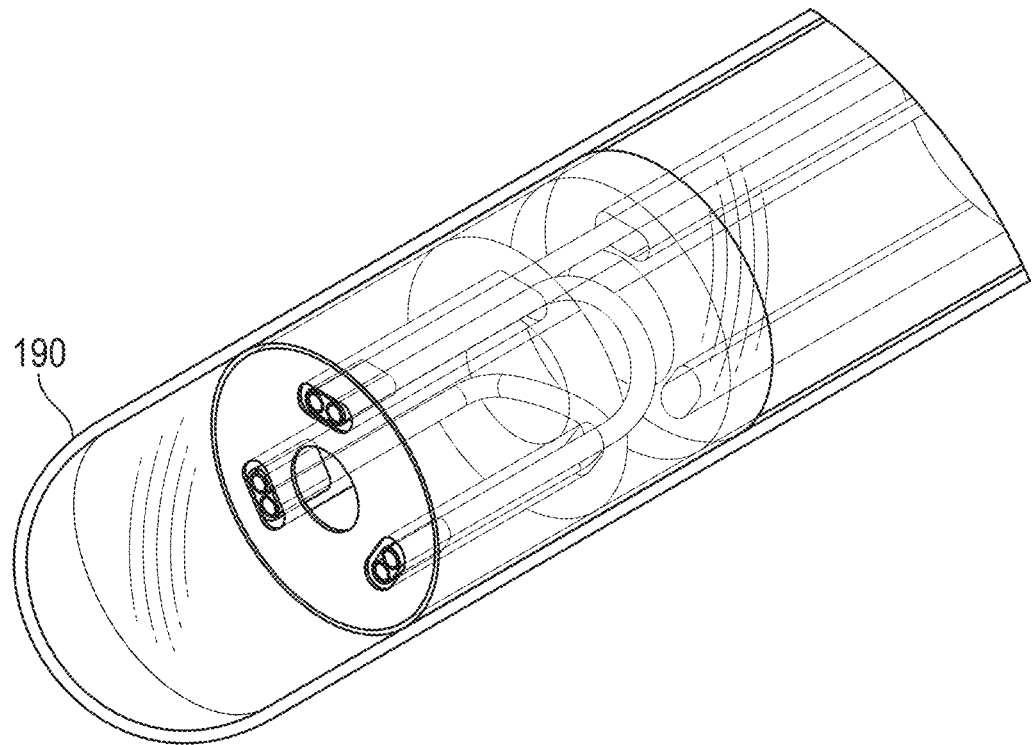
FIG. 2B illustrates an isometric view of a distal end of a catheter including a plurality of shock wave emitters encased in an enclosure, according to some embodiments.

In some embodiments the catheter 100 illustrated in FIGS. 1A-1D includes an enclosure 190 positioned to cover the plurality of shock wave emitters at the distal end 104 of the catheter body 101, as shown in FIGS. 2A and 2B. In some embodiments, the enclosure 190 is a cap, and in some embodiments, the enclosure 190 is an angioplasty balloon. In some embodiments, the enclosure 190 can be filled or inflated by pumping a conductive fluid, such as saline and/or contrast agent into the interior volume of the balloon. When attached, the enclosure may minimize the effect of negative pressures induced by cavitation bubbles that result from shock wave generation. As described above, without the enclosure, cavitation bubbles may exert tensile forces on a target treatment area when they collapse upon impact with the treatment area. However, with enclosure 190 attached and enclosing the shock wave emitters, the cavitation bubbles resulting from shock wave generation are separated from the target treatment area by the enclosure 190. Accordingly, the enclosure can protect soft tissue from potential damage resulting from the cavitation bubbles.

Figure 5:
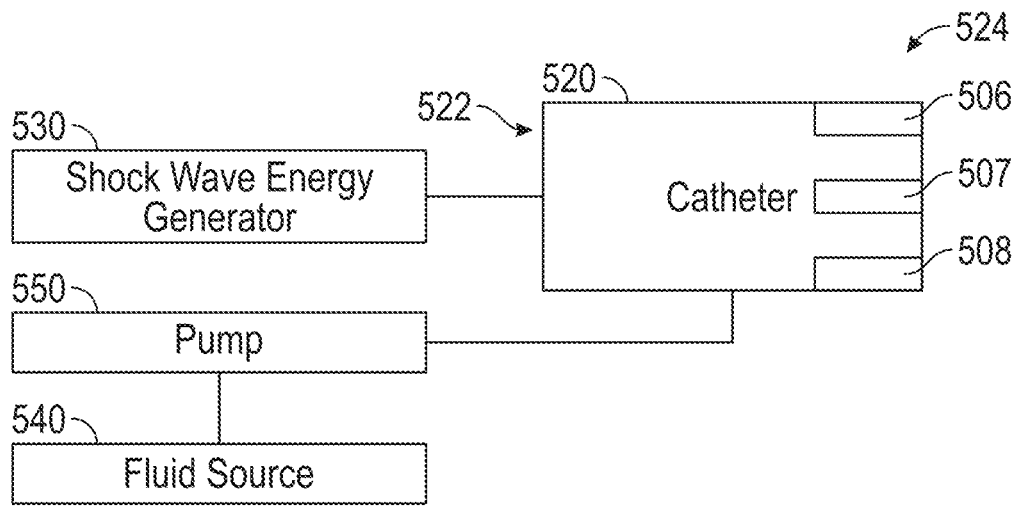
FIG. 5 illustrates a system for generating shock waves, according to some embodiments.

The enclosure 190 may be filled or inflated before, during, or after applying shock waves to a treatment region. For example, in some embodiments, after forward directed shock waves are initiated using the shock wave emitters 106-110 at the distal end 104 of the catheter 100 to break apart an occlusion, the catheter 100 is advanced further into a patient's vessel, and the enclosure 190 is inflated in the region of the occlusion to further treat the region. The conductive fluid may aid in cooling the device and dissipating heat generated during the formation of vapor bubbles that result from shock wave generation. The enclosure may also shield the shock wave emitters from direct contact with vessel walls and/or direct contact with an occlusion inside a body lumen. In some embodiments the enclosure 190 is formed of a thin, acoustically transparent material, such as polyethylene or nylon, which can provide for efficient fluid-to-tissue transmission and effective coupling of the pressure pulse from shock wave emitter to the occlusion or other calcification. In some embodiments, the catheter 100 may be connected to a fluid source 540 and fluid pump 550 (e.g., as shown in FIG. 5). The fluid pump 550 may fill the interior volume of the enclosure 190 with fluid to a certain pressure. The conductive fluid may be circulated within the interior volume of the enclosure 190 via a lumen of the catheter 100, for instance central lumen 150, by injecting the fluid into the enclosure 190 by a fluid pump 550 shown in FIG. 5 and drawing it into a fluid return line (not shown). In some embodiments, a conductive fluid is replenished (e.g., by continually flowing the conductive fluid into the enclosure 190 via a supply line, such as central lumen 150 or a different supply line, and allowing excess fluid to exit the enclosure 190 via a return line) during shock wave treatment to displace gas bubbles generated during shock wave emission. In some embodiments, instead of or in addition to a fluid pump, conductive fluid is supplied by a fluidically connected pressurized chamber (e.g., a saline bag). The method for replenishing conductive fluid described above may apply equally to any of the enclosures (e.g., 490, 790, 1290) included on any of the catheters described herein.

With respect to catheter 100 described above, the shock wave emitters are configured to respectively emit shock waves by creating a spark across a spark gap formed between the exposed distal ends of two wires. In some embodiments, such as the exemplary embodiment depicted in FIGS. 3A and 3B, the shock wave emitters may include conductive emitter bands. Shock waves may be generated by creating a spark across a spark gap between an exposed tip of a wire and a conductive emitter band. In some embodiments, the conductive emitter bands are conductive cylindrical tubes that at least partially circumscribe wires used to either generate shock waves and/or transfer current between multiple conductive emitter bands. Accordingly, in some embodiments, the shock wave emitters of the catheters described herein may include a respective conductive emitter band, a first insulated wire with an exposed distal tip positioned such that a spark gap is formed between the exposed distal tip and the conductive emitter band, and a second insulated wire that is electrically connected (e.g., soldered) to the conductive emitter band. The connected wire can be routed to a next shock wave emitter to transfer the electrical current from the first conductive emitter band to an electrode of the next shock wave emitter.

Figure 3A:
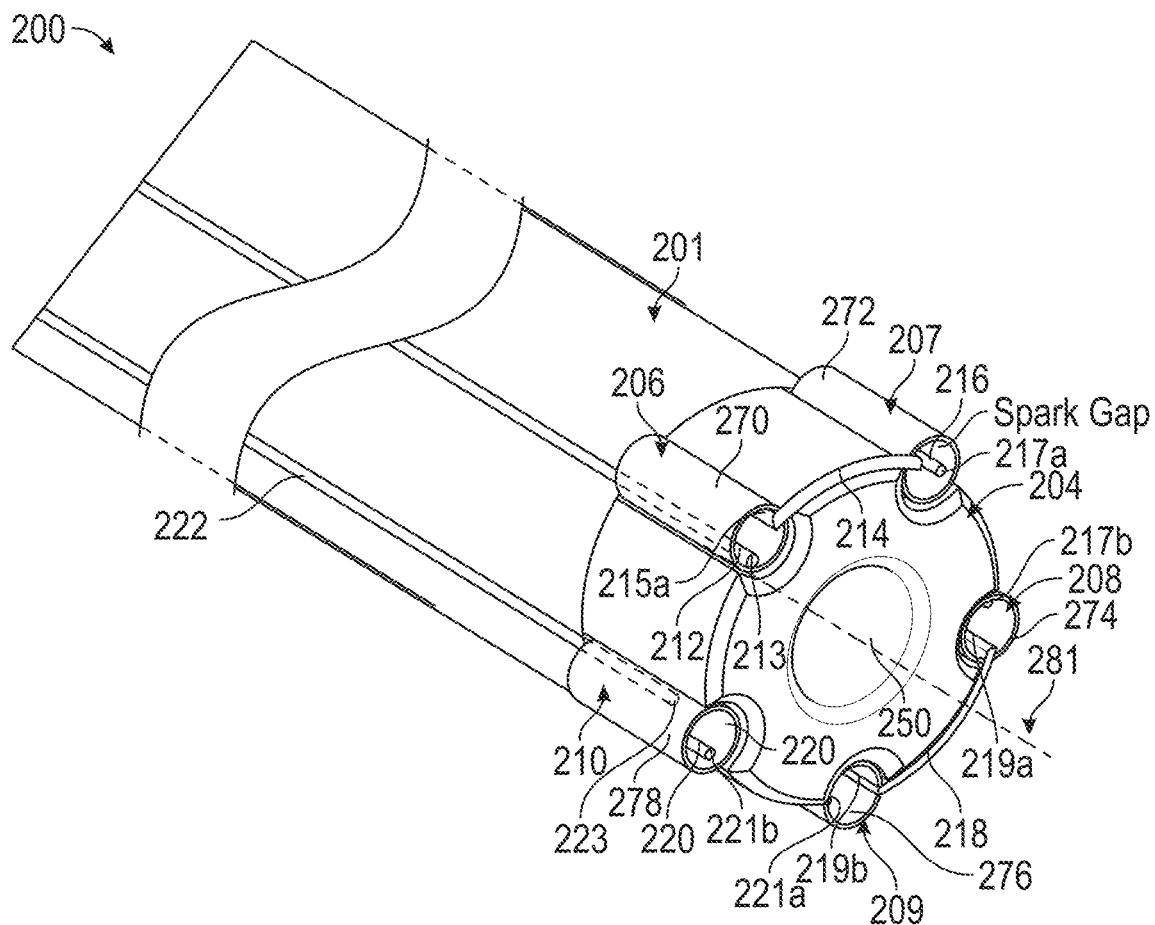
FIG. 3A illustrates an isometric view of a distal end of a catheter including a plurality of shock wave emitters, according to some embodiments.
Figure 3B:
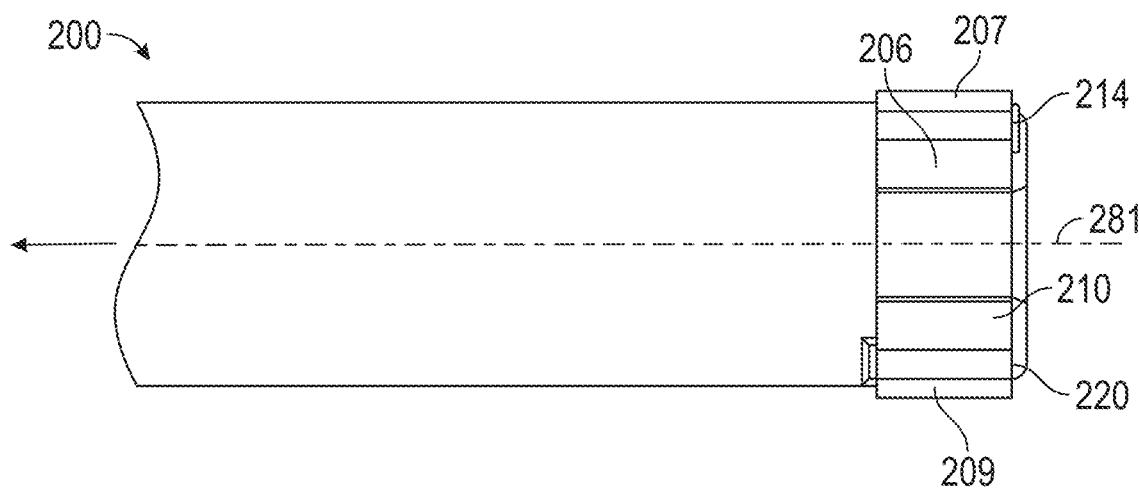
FIG. 3B illustrates a side view of a distal end of a catheter including a plurality of shock wave emitters, according to some embodiments.

FIGS. 3A and 3B illustrate an exemplary catheter 200 for generating shock waves in a forward direction that includes shock wave emitters formed by conductive emitter bands. Catheter 200 includes a catheter body 201 having a distal end 204. The catheter 200, as shown, includes a plurality of shock wave emitters 206-210 disposed at the distal end 204 of the catheter body 201. Each shock wave emitter 206-210 can be configured to generate a shock wave that propagates distally of the catheter body 201 (i.e., distally of distal end 204). The shock wave emitters 206-210 can be arrayed about a longitudinal axis of the catheter body 201 and configured such that shock waves emitted from the plurality of shock wave emitters 206-210 to constructively interfere distally of the catheter body 201. Thus, the positioning of the shock wave emitters 206-210 can maximize the shock wave intensity distally of the catheter body by causing shock waves emitted by each respective emitter to combine with one another to produce an amplified combined shock wave, for instance as illustrated in FIGS. 11A-11C.

FIGS. 3A and 3B illustrate an isometric view of the distal end 204 of catheter 200 and a side view of the distal end of catheter 200, respectively. In some embodiments, the shock wave emitters 206-210 of the catheter 200 shown in FIGS. 3A and 3B are electrically connected in series. Shock wave emitter 206 includes a conductive band 270 with a distal end and a proximal end, the distal end of the shock wave emitter 206 positioned relatively closer to the distal end 204 of the catheter body 201. The conductive band 270 may form an electrode pair with an exposed end 213 of a first insulated wire 212, the exposed end 213 positioned at the distal end of conductive band 270. The insulated wire 212 may be positioned within the conductive band 270 and separated by a spark gap from the conductive band 270 for generating shock waves when a voltage is applied across the spark gap. In some embodiments, the insulated wire 212 extends along the length of catheter body 201 from within the conductive band 270 at the distal end 204 such that the first insulated wire 212 can be connected to a voltage source.

In some embodiments, shock wave emitter 206 includes a second insulated wire 214 with a first exposed end 215a electrically connected (e.g., may be soldered, crimped, taped, adhered, clamped, or otherwise electrically connected to) to the conductive emitter band 270. In some embodiments, the insulated wire 214 is disposed at least partially within the interior of conductive emitter band 270 and the exposed end 215a is electrically connected (e.g., may be soldered, crimped, tapes, clamped, or otherwise connected to) to an inner surface of the conductive band 270. It should be understood, however, that the exposed end 215a could be electrically connected to any conductive surface of the conductive band 270. In some embodiments, a second exposed end (not shown) of the second insulated wire 214 is electrically connected to a conductive band 272 of a second shock wave emitter 207 to transfer the voltage between the conductive band 270 of the first shock wave emitter 206 and the conductive band 272 of the second shock wave emitter 207. Similar to conductive band 270, the conductive band 272 has a distal end and a proximal end, the distal end of the conductive band 272 positioned relatively closer to the distal end 204 of the catheter body 201. Shock wave emitter 207 includes a first exposed tip 217a of a third insulated wire 216 positioned at least partially within the interior of conductive emitter band 272, the exposed tip 271a positioned at the distal end of the conductive emitter band 272 such that shock waves generated by the shock wave emitter 207 propagate distally. Insulated wire 216 is positioned to form a spark gap between the exposed tip 217a and the conductive emitter band 272 such that an electrical current can flow between the conductive emitter band 272 and the exposed tip 217a to generate a shock wave distally of the distal end of the catheter body 201.

Insulated wire 216 is also positioned to transfer current from the second shock wave emitter 207 to a third shock wave emitter 208, and a spark gap is formed between a second exposed end 217b of insulated wire 216 and a conductive band 274 at the distal end of the conductive emitter band, as described below. Specifically, insulated wire 216 is inserted into both conductive bands 272 and 274 from the proximal end of each conductive band such that a portion of insulated wire 216 extends into both conductive bands 272 and 274 toward the distal end of each respective conductive emitter band. Insulated wire 216 includes a second exposed end 217b disposed at the distal end of the conductive emitter 274. Insulated wire 216 is positioned such that a spark gap separates the second exposed end 217b from the conductive band 274. Accordingly, when an electrical current flows between exposed end 217b and conductive band 274 another shock wave is generated at shock wave emitter 208 and propagates distally of the shock wave emitter 208.

In some embodiments, a first exposed end 219a of a fourth insulated wire 218 is electrically connected (e.g., may be soldered, crimped, tapes, clamped, or otherwise electrically connected to) to the conductive band 274. In some embodiments, the insulated wire 218 is positioned at least partially within the interior of conductive band 274 and the exposed end 219a is electrically connected (e.g., may be soldered, crimped, tapes, clamped, or otherwise electrically connected to) to an inner surface of the conductive band. As with shock wave emitters 206 and 207, it should be understood that the exposed end 219a could be electrically connected to any conductive surface of the conductive band 274. In some embodiments, a second exposed end 219b of the second insulated wire 218 is electrically connected to a conductive band 276 of a fourth shock wave emitter 209 to transfer the electrical current between the conductive band 274 of the third shock wave emitter 208 and the conductive band 276 of the fourth shock wave emitter 209. More specifically, similar to conductive band 270, 272, and 274, the conductive band 276 has a distal end and a proximal end, the distal end positioned relatively closer to the distal end 204 of the catheter body 201. Insulated wire 218 may extend outwardly from the distal end of the conductive emitter band 274 and exit the conductive emitter band 274 from its distal end. Insulated wire 218 may then be directed toward the next shock wave emitter in the series, shock wave emitter 209. Insulated wire 218 may extend into the distal end of conductive band 276 and a second exposed end 219b of insulated wire 218 may be electrically connected to the conductive band 276 to transfer an electrical current between the conductive band 274 of the third shock wave emitter 208 and the conductive band 276 of the fourth shock wave emitter 209.

Shock wave emitter 209 additionally includes a first exposed end 221a of a fifth insulated wire 220. The fifth insulated wire is disposed at least partially within the interior of conductive band 276, and the first exposed end 221a is disposed at the distal end of the conductive emitter band 276. Insulated wire 220 is positioned within conductive emitter band 276 such that the exposed end 221a is separated by a spark gap from the conductive emitter band 276. Accordingly, when a current flows across the spark gap between the conductive emitter band 276 and the exposed end 221a a spark is created thus generating a shock wave that propagates distally of the distal end of the catheter body 201.

Similar to insulated wire 216, in some embodiments, the insulated wire 220 is routed to a fifth shock wave emitter 210 and an exposed end 221b of wire 220 is separated by a spark gap from a conductive band 278 at the distal end of the conductive emitter band, as described in more detail below. Insulated wire 220 may be inserted into both conductive bands 276 and 278 from the proximal end of each respective conductive band. A portion of insulated wire 220 extends into both conductive bands 276 and 278 toward the distal end of each respective conductive emitter band, for instance, as shown in the side view of catheter 200 in FIG. 3B. Insulated wire 220 may include a second exposed end 221b positioned at the distal end of the conductive emitter band 278 (i.e., the end of the conductive emitter band facing the distal end of catheter body 201), as described above. The insulated wire 220 may be positioned such that the exposed end 221b is separated by a spark gap from the conductive emitter band 278. Accordingly, when the current flows between the exposed tip 221b to conductive emitter band 278 a shock wave is generated by shock wave emitter 210. A sixth insulated wire 222 with an exposed tip 223 may be electrically connected (e.g., soldered crimped, tapes, clamped, or otherwise electrically connected to) to the conductive emitter band 278 and may extend along the length of the catheter body 201 from the conductive emitter band 278 at the distal end 204 to connect to a positive terminal of a voltage source. Accordingly, when a voltage is applied across the negative and positive terminal, and thus across wires 212 and 222, a plurality of shock waves are generated at each of the shock wave emitters 206-210.

In some embodiments, each of the respective shock wave emitters 206-210 are positioned within a respective cavity 240 formed into the outer circumferential surface of catheter body 201. In some embodiments, each cavity 240 has a semi-circular shape sized such that a respective conductive emitter 270-278 band having a cylindrical shape can be positioned at least partially within a semi-circular cavity 240. In some embodiments, each cavity 240 extends along the length of catheter body 201 from distal end 204 (e.g., to a proximal end of the catheter body 201). In some embodiments, one or more of the insulated wires included in shock wave emitters 206-210 extend within a respective cavity 240 along the length of the catheter body 201 to connect to a voltage source.

In some embodiments, the catheter 200 includes a central lumen 250 extending from the distal end 204 along the length of the catheter body 201. The central lumen 250 may be configured to receive a guide wire. For instance, the guide wire can be inserted into the catheter 200 via central lumen 250 proximally of the distal end 204 and exit the catheter via the central lumen 250 at the distal end 204. The guide wire can be used to guide the catheter into place within a body lumen (e.g., blood vessel or other organ). In some embodiments, the central lumen 250, like central lumen 150 of catheter 100, is configured to receive a pacemaker wire lead at the distal end 204 of the catheter body 201 for removing the pacemaker wire lead from a tissue, such as cardiac tissue (for instance, as illustrated in FIG. 9, below). In some embodiments, the catheter body 201 includes an aspiration lumen. In some embodiments, the aspiration lumen is for removing debris from a body lumen. In some embodiments central lumen 250 can be configured for aspiration. In some embodiments, the catheter body may include a separate lumen (not shown) for aspiration. In some embodiments, the catheter 100 includes a marker band for determining an orientation of the catheter within a body lumen.

Although catheter 200 is described as having five shock wave emitters electrically connected in series such that an electrical pulse applied to a first shock wave emitter of the plurality of shock wave emitters causes each of the plurality of shock wave emitters to emit a respective shock wave, it should be understood that the shock wave emitters could be configured such that any of the shock wave emitters of the plurality of shock wave emitters 206-210 can be driven independently of any of the other shock wave emitter of the plurality of shock wave emitters. An exemplary embodiment illustrating a catheter including a first set of shock wave emitters configured to be driven independently of one another and a second set of shock wave emitters configured to be driven in series is illustrated below in FIG. 10.

In the exemplary embodiment depicted in FIGS. 3A and 3B, the plurality of shock wave emitters 206-210 of catheter 200 are arrayed symmetrically about the longitudinal axis 281 of the catheter body and a distal most surface of each of shock wave emitters 206-210 is positioned such that it is recessed from a distal most surface of the distal end 204 of the catheter body 201. However, it should be understood that the plurality of shock wave emitters on the catheters described herein (e.g., catheter 100 and catheter 200) could be arranged in a variety of configurations without deviating from the scope of the claims, for instance, as shown in the exemplary embodiments depicted in FIGS. 4A-4E. It should be understood that any of the features illustrated in FIGS. 4A-4E with respect to catheters 400a-400e are equally applicable to catheters 100 and 200 described above and are not in any way meant to be limiting.

FIG. 4A illustrates a front view of a catheter 400a, in accordance with some embodiments. Catheter 400a includes a plurality of shock wave emitters 406a-409a arrayed asymmetrically about longitudinal axis 481 of catheter 400a. An outer surface of each of shock wave emitters 406a-409a is flush with an outer circumferential surface a catheter body 401 of the catheter 400. FIG. 4B illustrates a front view of a catheter 400b, in accordance with some embodiments. Catheter 400b similarly includes a plurality of shock wave emitters 406b-408b also arrayed asymmetrically about longitudinal axis 481 of catheter 400b. Shock wave emitter 406b is positioned such that its outer circumferential surface is positioned externally relative an outer circumferential surface of the catheter body 401b, shock wave emitter 407b is positioned such that its outer circumferential surface is positioned inset relative an outer circumferential surface of the catheter body 401b, and shock wave emitter 408b is positioned such that its outer circumferential surface is flush with an outer circumferential surface of the catheter body 401b.

FIGS. 4C-4E illustrate a side view of catheters 400c-400e, respectively, in accordance with some embodiments. Catheter 400c depicted in FIG. 4C includes a plurality of shock wave emitters 406c-408c at a distal end 404 of the catheter body 401. Shock wave emitters 406c-408c are positioned such that a distal most surface of each of shock wave emitters 406c-408c is positioned forward of a distal most surface of the distal end 404 of the catheter body 201. All of shock wave emitters 406c-408c are further positioned at the same distal location relative to the distal most surface of the catheter body 401. Shock wave emitters 406c-408c may be arrayed symmetrically or asymmetrically about the longitudinal axis 481 of the catheter body 401. Catheter 400d of FIG. 4D includes a plurality of shock wave emitters 406d-408d at the distal end of catheter body 401. Shock wave emitters 406d-408d are positioned such that a distal most surface of each of shock wave emitters 406d and 408d is forward of the distal most surface of catheter body 401 and shock wave emitter 407d is positioned such that a distal most surface of shock wave emitter 407d is recessed from a distal most surface of the catheter body 401.

FIG. 4E illustrates a side view of catheter 400e, which includes a plurality of shock wave emitters 406e-408e at a distal end 404 of the catheter body 401. Catheter 400e further includes an enclosure 490 positioned to cover the plurality of shock wave emitters 406e-408e. The enclosure 490 may include any of the characteristics described above with reference to enclosure 190. Accordingly, in some embodiments, the enclosure 490 is a cap or an angioplasty balloon. In some embodiments, the enclosure 490 can be filled or inflated by pumping a conductive fluid, such as saline and/or contrast agent into the interior volume of the balloon. The enclosure 490 may be inflated before or after applying shock waves to a treatment region. For example, in some embodiments, after forward directed shock waves are initiated using the shock wave emitters 406e-408e at the distal end 404 of the catheter 400e to break apart an occlusion, the catheter 400e is advanced further into a patient's vessel, and the enclosure 490 is inflated in the region of the occlusion to further treat the region. The conductive fluid may aid in cooling the device and dissipating heat generated during the formation of vapor bubbles that result from shock wave generation. The enclosure may also shield the shock wave emitters from direct contact with vessel walls and/or direct contact with an occlusion inside a body lumen. In some embodiments the enclosure 490 is formed of a thin, acoustically transparent material, such as polyethylene or nylon, which can provide for efficient fluid-to-tissue transmission and effective coupling of the pressure pulse from shock wave emitter to the occlusion or other calcification. While the enclosure is only illustrated with respect to the exemplary catheter shown in FIG. 4E, it should be understood that a similar enclosure could optionally be provided on any of catheters 4A-4D, or any of the other catheters described herein. Alternatively, any of the embodiments described herein may be configured as an open system (i.e., there may be no enclosure surrounding the shock wave emitters provided on any of the catheters described herein).

As described above, the exemplary catheters described herein may be connected to a voltage source and fluid source. The voltage source may be connected to one or more of the wires used to generate shock waves at the plurality of shock wave emitters of the catheters described herein, and the fluid source may be used to fill portions of the catheter, such as enclosure 190 and 490, with a conductive fluid, as described above.

FIG. 5 illustrates an exemplary system 500 comprising a catheter 520 connected to a shock wave energy generator 530. In some embodiments, catheter 520 may include any combination of the features described above with reference to FIGS. 1A-4E above, and/or FIGS. 7A-11C below. Accordingly, in some embodiments, catheter 520 includes a plurality of shock wave emitters 506-508 at a distal end 524 of catheter 520. In some embodiments, the plurality of shock wave emitters 506-508 include laser emitters, and a plurality of optical fibers extend along the length of the catheter 520 from the emitters 506-508 to the shock wave energy generator 530. In some embodiments, catheter 520 is connected to one or both of the shock wave energy generator 530 and/or fluid source 540 at proximal end 522 of the catheter 520.

In some embodiments, shock wave energy generator 530 is a portable and/or rechargeable voltage source. In some embodiments shock wave energy generator 530 is a laser pulse generator. In some embodiments, shock wave energy generator 530 is configured to deliver high voltage pulses to a shock wave emitter of a plurality of shock wave emitters of catheter 520, wherein the high voltage pulses are between 3 kV and 20 kV, including 3 kV and 20 kV. In some embodiments, the high voltage pulses are between 10 kV and 20 kV, including 10 kV and 20 kV. In some embodiments, the high voltage pulses are between 15 kV and 20 kV, including 15 kV and 20 kV. In some embodiments, the high voltage pulses are greater than 20 kV. The high voltage pulses may be at least 1 kV, at least 2 kV, at least 3 kV, at least 4 kV, at least 5 kV, at least 6 kV, at least 7 kV, at least 8 kV, at least 9 kV, at least 10 kV, at least 11 kV, at least 12 kV, at least 13 kV, at least 14 kV, at least 15 kV, at least 16 kV, at least 17 kV, at least 18 kV, at least 19 kV, and/or at least 20 kV. The high voltage pulses may be no more than 20 kV, no more than 19 kV, no more than 18 kV, no more than 17 kV, no more than 16 kV, no more than 15 kV, no more than 14 kV, no more than 13 kV, no more than 12 kV, no more than 11 kV, no more than 10 kV, no more than 9 kV, no more than 8 kV, no more than 7 kV, no more than 6 kV, no more than 5 kV, no more than 4 kV, no more than 3 kV, no more than 2 kV, and/or no more than 1 kV.

In some embodiments, shock wave energy generator 530 is configured to deliver the voltage pulses at a rate of between 1 Hz and 100 Hz, including 1 Hz and 100 Hz. In some embodiments, shock wave energy generator 530 is configured to deliver the voltage pulses at a rate of a rate of between 1 Hz and 50 Hz, including 1 Hz and 50 Hz. Shock wave energy generator 530 may be configured to deliver the voltage pulses at a rate of a rate of up to 100 Hz, up to 90 Hz, up to 80 Hz, up to 70 Hz, up to 60 Hz, up to 50 Hz, up to 40 Hz, up to 30 Hz, up to 20 Hz, and/or up to 10 Hz. Shock wave energy generator 530 may be configured to deliver the voltage pulses at a rate of at least 10 Hz, at least 20 Hz, at least 30 Hz, at least 40 Hz, at least 50 Hz, at least 60 Hz, at least 70 Hz, at least 80 Hz, at least 90 Hz, and/or at least 100 Hz. In some embodiments, shock wave energy generator 530 is configured to deliver the voltage pulses at a rate of a rate of up to 20 Hz, including at a rate of 20 Hz. In some embodiments, shock wave energy generator 530 can be configured to apply an alternating current to the electrodes of the shock wave emitters to induce a change in the polarity of the electrodes.

In some embodiments, catheter 520 is connected to fluid source 540 using a pump 550. In some embodiments, the fluid source 540 may contain a conductive fluid such as saline and/or contrast agent that can be injected into catheter 520 using the pump 550. As described above, the conductive fluid injected into catheter 520 may be used to fill an inflatable enclosure, such as a cap or an angioplasty balloon. The conductive fluid may aid in cooling the device and dissipating heat generated during the formation of vapor bubbles that result from shock wave generation. The enclosure may also shield the shock wave emitters from direct contact with vessel walls and/or direct contact with an occlusion inside a body lumen.

Figure 6:
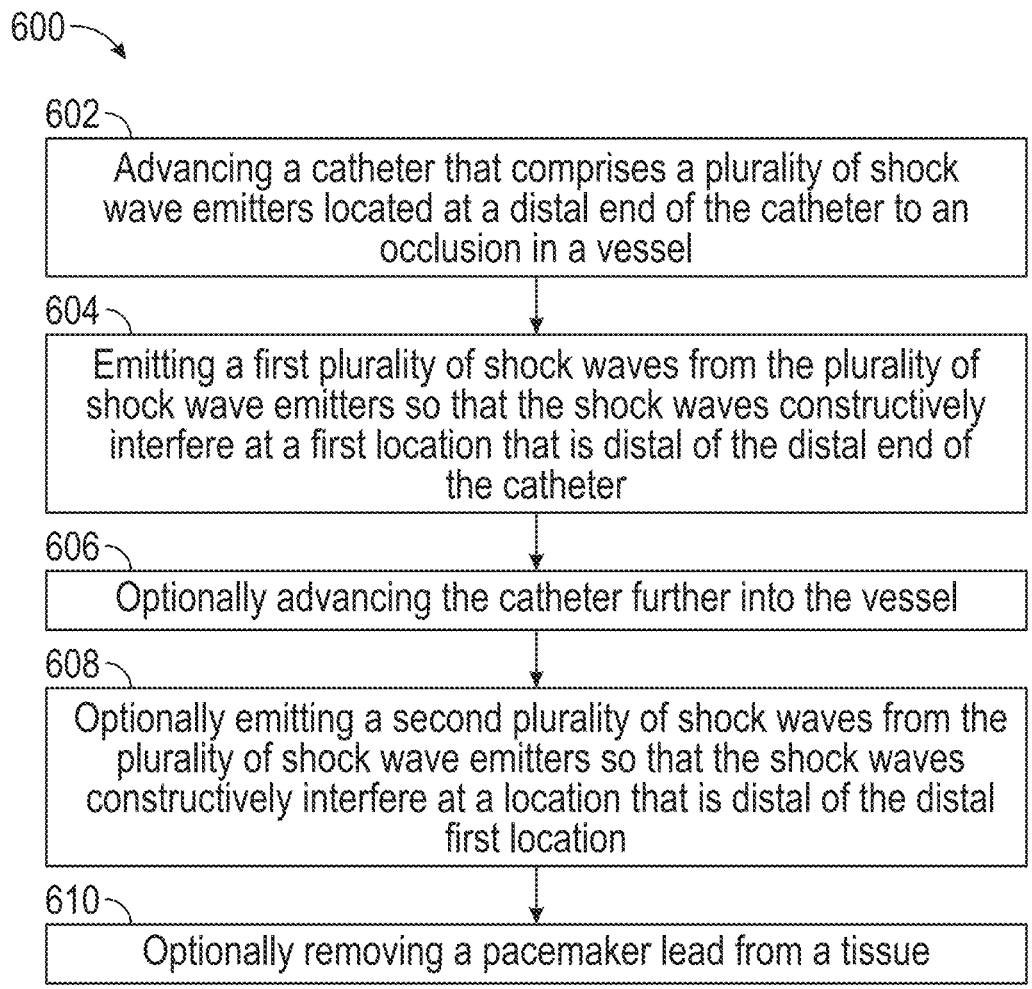
FIG. 6 illustrates a method for emitting shock waves in a vessel, according to some embodiments.

The catheters described herein may be used for treating various calcifications within a human body lumen, according to some embodiments. For instance, the shock waves generated by any of catheters 100, 200, 400a-400e, and/or 520 may be used to crack, fragment, or otherwise break up calcifications such as kidney stones and/or occlusions within a blood vessel. FIG. 6 illustrates an exemplary method for emitting shock waves in a body lumen, according to some embodiments.

At block 602, an exemplary catheter that includes a plurality of shock wave emitters located at a distal end of the catheter body is positioned adjacent to an occlusion in a vessel. The vessel may include blood vessels in a patient's vascular system or ureters in the patient's urinary system. The catheter may be any of catheters 100, 200, 400a-e, or 500 described above, and/or any of catheters 700a-700b, 800a-800c, 900, 1000, and/or 1100a-1100c below. The shock wave device is positioned within the vessel such that a distal end of the device faces a first treatment region. The first treatment region may include a chronic total occlusion (CTO), circumferential calcium, a kidney stone, or other obstructions or concretions. Once the distal end of the shock wave device is facing the first treatment region, the method 600 can proceed to block 604. In some embodiments, the first treatment region may include fibrotic/calcified cardiac tissue surrounding a pacemaker lead, and the catheter may be positioned such that a lumen of the catheter body surrounds the pacemaker lead, for instance as shown in FIG. 9.

At block 604, the catheter emits a first plurality of shock waves from the plurality of shock wave emitters in a distal direction so that the shock waves constructively interfere distally of the distal end of the catheter. As described above, the shock waves may be generated by applying a voltage across a plurality of electrode pairs, each separated by a spark gap. A spark is generated as a current flows between the electrodes of the electrode pair across the spark gap, which generates a shock wave. This shock wave generation process may occur simultaneously across a plurality of shock wave emitters connected in series and/or shock waves may be generated at one or more shock wave emitters configured to generate shock waves independently of the other emitters. Due to the positioning of the shock wave emitters, the plurality of shock waves propagate in a substantially forward direction out of the catheter to constructively interfere with one another and impinge on the occlusion or calcium in the first treatment area.

At block 606, the catheter is optionally advanced further into the blood vessel, for instance, if the first plurality of shock waves did not successfully break up the entire occlusion. At block 608, the catheter optionally emits a second plurality of shock waves from the plurality of shock wave emitters so that the shock waves constructively interfere at a location that is distal of the first location. Blocks 606 and 608 may be iteratively repeated until the occlusion has been successfully treated. At block 610, the catheter is optionally used to remove a pacemaker lead from a cardiac tissue. As noted above, the pacemaker lead may be inserted into a lumen of the catheter body. The shock waves emitted by the plurality of shock wave emitters may fragment/break up fibrotic/calcified tissue around the pacemaker lead, allowing the pacemaker lead to be removed by withdrawing the catheter away from the treatment area. It should be understood that the aforementioned steps do not need be performed in the order presented, and some steps may be omitted altogether. For instance, the pacemaker lead may be removed immediately following the initial plurality of shock waves generated at step 604 and a second plurality of shock waves may not be emitted from the catheter.

Figure 7A:
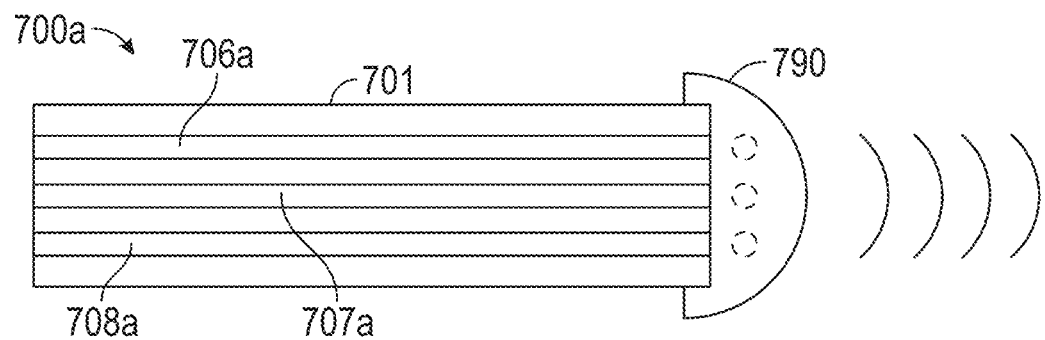
FIGS. 7A-7B illustrate the effect of various embodiments of an enclosure such as a cap or angioplasty balloon enclosing shock wave emitters on shock wave propagation.
Figure 7B:
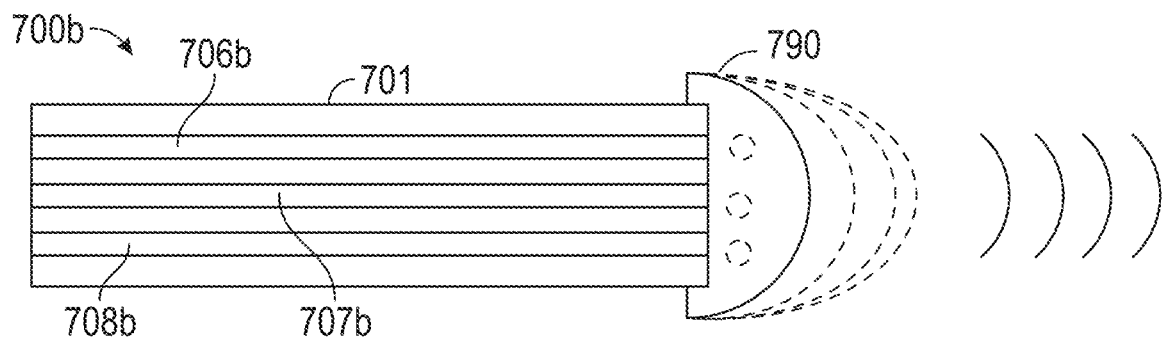

As described throughout, the catheters described herein may include an enclosure that provides a protective barrier between the shock wave emitters and soft tissue within the body by mitigating thermal injury to soft tissue and reducing cavitation stresses by limiting expansion of the vapor bubble to the interior of the cap. FIG. 7A illustrates the impact of an enclosure 790 disposed at a distal end of a catheter body 701, encasing shock wave emitters 706a-708a impacts the propagation of cavitation bubbles distally of the distal end of the catheter body 701. As shown, the vapor bubbles hit the wall of enclosure 790 before reaching their maximum potential size, thus inducing collapse preventing potential soft tissue injury that can be caused by tensile stresses resulting from the collapse of the bubbles outside of the enclosure 790. In the embodiment illustrated in FIG. 7A, the enclosure 790 is approximately semi-cylindrical or semi-spherical in shape. FIG. 7B illustrates that various differently shaped caps could be used in place of the semi-cylindrical or semi-spherical shape, for instance enclosure with either greater or less elongation distally of the distal end of the catheter body 701b. In some embodiments, an enclosure having greater elongation distally of distal end of the catheter body 701b (i.e., having a narrower parabolic shape) may result in shock waves emitted from the shock wave emitters and catheter having a correspondingly narrower parabolic shape. In some embodiments, an enclosure having less elongation distally of distal end of the catheter body 701b (i.e., having a wider parabolic shape) may result in shock waves emitted from the shock wave emitters having a correspondingly wider parabolic shape.

Figure 8A:
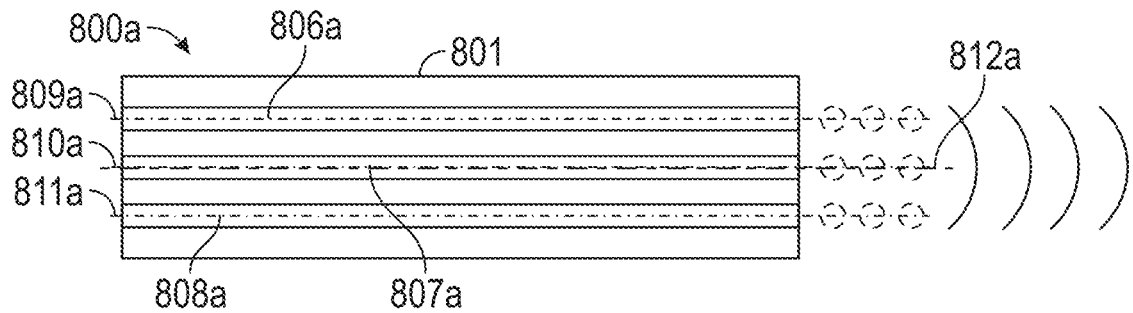
FIGS. 8A-8C illustrate directional control of shock waves using different shock wave emitter and catheter body configurations.
Figure 8B:
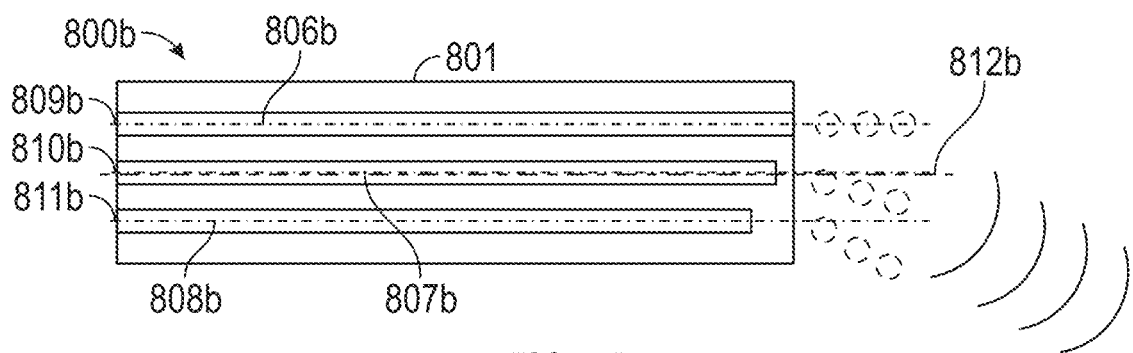
Figure 8C:
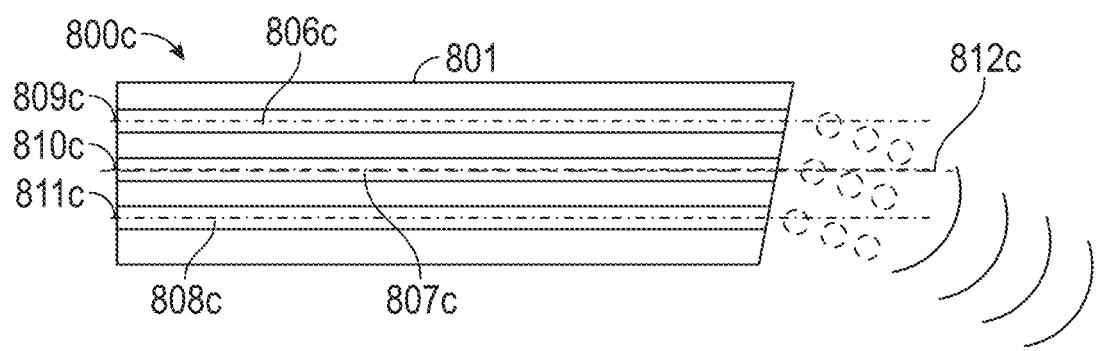

In some embodiments, no enclosure is provided on the catheters described herein. In such embodiments, it may be desirable to exercise greater control over the direction of shock wave and/or cavitation bubble propagation to direct cavitation bubbles and shock waves away from soft tissue and toward target treatment areas. FIGS. 4A-4D described above illustrated various options for arranging shock wave emitters at the distal end of a catheter. FIGS. 8A-8C described below further illustrate how both the arrangement of emitters and the shape of the catheter body itself can impact the manner in which shock waves propagate distally of the distal end of the catheter body. In some embodiments, positioning shock wave emitters such that their distal most surface is recessed from a distal most surface of the catheter body (i.e., into the catheter body may cause the recessed shock wave emitter to generate cavitation bubbles and corresponding shock waves that propagate at an angle diverging from the longitudinal axis of the shock wave emitter and/or the longitudinal axis of the catheter body. In some embodiments, configuring the distal most surface of the catheter body such that it is slanted (i.e., not perpendicular to the longitudinal axis of the catheter body) may cause cavitation bubbles and corresponding shock waves generated by the shock wave emitters to propagate at an angle diverging from the longitudinal axis of the catheter body.

FIG. 8A illustrates a side view of catheter 800a including a plurality of shock wave emitters 806a-808a at a distal end of a catheter body 801. Each of shock wave emitters 806a-808a are positioned such that a distal most surface of each shock wave emitter is respectively positioned flush with a flat (i.e., perpendicular to a longitudinal axis 812a of the catheter body 801) distal most surface 804a of catheter body 801. In some embodiments, the distal most ends of each emitter are coplanar with each other and/or a distal most edge surface of the catheter body. In some embodiments, one or more shock wave emitters have distal most ends that extend no more than 0.5 mm longitudinally from a flat distal most surface of the catheter body. In some embodiments, one or more shock wave emitters have distal most ends that extend no more than 0.1 mm, no more than 0.2 mm, no more than 0.3 mm, no more than 0.4 mm, no more than 0.5 mm, no more than 0.6 mm, no more than 0.7 mm, no more than 0.8 mm, no more than 0.9 mm, or no more than 1.0 mm longitudinally from a flat distal most surface of the catheter body. In some embodiments, one or more shock wave emitters have distal most ends that extend at least 0.1 mm, at least 0.2 mm, at least 0.3 mm, at least 0.4 mm, at least 0.5 mm, at least 0.6 mm, at least 0.7 mm, at least 0.8 mm, at least 0.9 mm, or at least 1.0 mm. In some embodiments, one or more shock wave emitters have distal most ends that extend between 0.01 mm and 1.0 mm longitudinally from a flat distal most surface of the catheter body. In some embodiments, positioning a distal most surface of the shock wave emitters flush with a flat distal most surface $804a$ of the catheter body may result in cavitation bubbles that propagate distally of the distal end of the catheter body 801 along each of the respective longitudinal axes ($809a$, $810a$, and $811a$) of the plurality of shock wave emitters. The cavitation bubbles may collapse distally of the distal end of catheter body 801, resulting in corresponding constructively interfering shock waves that propagate forward in a unitary direction, as illustrated. In some embodiments, such a configuration of both the shock wave emitters and the catheter body may result in cavitation bubbles that propagate distally of the distal end of catheter body 801 in a direction parallel with the longitudinal axis $812a$ of the catheter body 801.

FIG. 8B illustrates that positioning shock wave emitters $806b$-$808b$ in a staggered formation relative to a flat distal most surface $804b$ of catheter body 801 may enable directional control of shock waves. In the embodiment of FIG. 8B, a distal most surface of shock wave emitter $806b$ is positioned flush with a distal most surface $804b$ of catheter body 801, a distal most surface of shock wave emitter $807b$ is recessed a first distance from the distal most surface $804b$ of catheter body 801, and a distal most surface of shock wave emitter $808b$ is recessed a second distance, greater than the first distance, from the distal most surface $804b$ of catheter body 801. As described above with reference to FIG. 8A, shock wave emitter $806b$ may produce cavitation bubbles that propagate distally of the distal end of the catheter body 801 along the longitudinal axis $809b$ of shock wave emitter $806b$. In contrast, the positioning of shock wave emitters $807b$ and $808b$ may result in cavitation bubbles that propagate distally of the distal end of the catheter body 801 at respective angles relative to the longitudinal axes of shock wave emitters $807b$ and $808b$, such that the cavitation bubbles diverge from the longitudinal axes $810b$ and $811b$, respectively, of shock wave emitters $807b$ and $808b$. In some embodiments, the recession of the distal most surface of a shock wave emitter further into the catheter body 801 may result in cavitation bubbles that diverge further (i.e., at an angle greater in magnitude) from the longitudinal axis of the respective shock wave emitter. In some embodiments, the shock waves resulting from collapse of the cavitation bubbles may constructively interfere with one another and propagate forward at an angle relative to the longitudinal axis $812b$ of catheter body 801, wherein the direction of propagation of the constructively interfering shock waves is based on the respective direction of propagation of the cavitation bubbles generated by each of the shock wave emitters.

FIG. 8C illustrates that the shape of the catheter body may also be configured to enable directional control of shock waves. In the embodiment of FIG. 8C, a distal most surface $804c$ of catheter body 801 is slanted, rather than perpendicular to a longitudinal axis $812c$ of the catheter body 801 (i.e., configured such that a plane corresponding to the distal most surface $804c$ intersects a plane corresponding to the longitudinal axis 812 of catheter body 801 at an angle greater than or less than 90 degrees). The catheter $800c$ of FIG. 8C includes a plurality of shock wave emitters $806c$-$808c$. The shock wave emitters $806c$-$808c$ are positioned such that a distal most surface of each shock wave emitter is positioned at a different distal location relative to each of the other shock wave emitters. In the embodiment of FIG. 8C, a distal most surface of shock wave emitter $806c$ is positioned at a first location relative to a proximal end of catheter body 801, a distal most surface of shock wave emitter $807c$ is positioned at a second location relative to the distal most surface of shock wave emitter $806c$, and a distal most surface of shock wave emitter $808c$ is positioned at a third location relative to the distal most surfaces of both shock wave emitters $806c$ and $807c$. Optionally, the distal most surface of each of the shock wave emitters $806c$-$808c$ may be positioned flush with the distal most surface $804c$ of catheter body 801.

The relative positioning of shock wave emitters $806c$-$808c$ and the slanted distal most surface $804c$ of catheter body 801 may result in cavitation bubbles generated by each of the shock wave emitters that propagate distally of the distal end of the catheter body 801 parallel to one another at an angle diverging from each of their respective longitudinal axes $809c$, $810c$, and $811c$. Thus, the cavitation bubbles generated by each of the shock wave emitters $806c$-$808c$ propagate parallel to one another at the same angle diverging from the longitudinal axis $812c$ of the catheter body 801, and accordingly, the shock waves resulting from collapse of the cavitation bubbles may constructively interfere with one another and propagate forward in the same direction as the cavitation bubbles relative to the longitudinal axis $812c$ of catheter body 801.

As described above, the catheters described herein may be useful for pacemaker lead removal. Cardiac tissue surrounding pacemaker leads inserted into the tissue can become calcified/fibrotic over time, making it difficult to remove the leads. Shock wave treatment can break up the calcified/fibrotic tissue, thus loosening the attachment between the tissue and the pacemaker leads and enabling easier removal of the leads. FIG. 9 illustrates an exemplary catheter 900 including a plurality of shock wave emitters and a lumen 904 for removing a pacemaker lead 906 from cardiac tissue 908. The catheter 900 may be positioned within a vessel such that pacemaker lead 906 is inserted into lumen 904. Pacemaker lead 906 may thus act as a guidewire for catheter 900, enabling a user to advance the catheter to a point of attachment between the pacemaker lead and cardiac tissue (e.g., heart muscle). When the catheter is positioned such that the shock wave emitters are adjacent to and facing the calcified/fibrotic tissue 910, a plurality of shock waves can be generated (as described herein) to break up the calcified/fibrotic tissue 910 and loosen the pacemaker lead. If the first plurality of shock waves do not free the pacemaker lead from the tissue, the catheter 900 can optionally be advanced further toward the calcified/fibrotic tissue 910 and/or a second plurality of shock waves can be generated. This process can be repeated as needed until the attachment between the pacemaker lead and cardiac tissue is sufficiently loosened such that the pacemaker lead can be removed either by removing the catheter along with the pacemaker lead, or by removing the catheter and inserting a separate tool for pacemaker lead removal.

Figure 10:
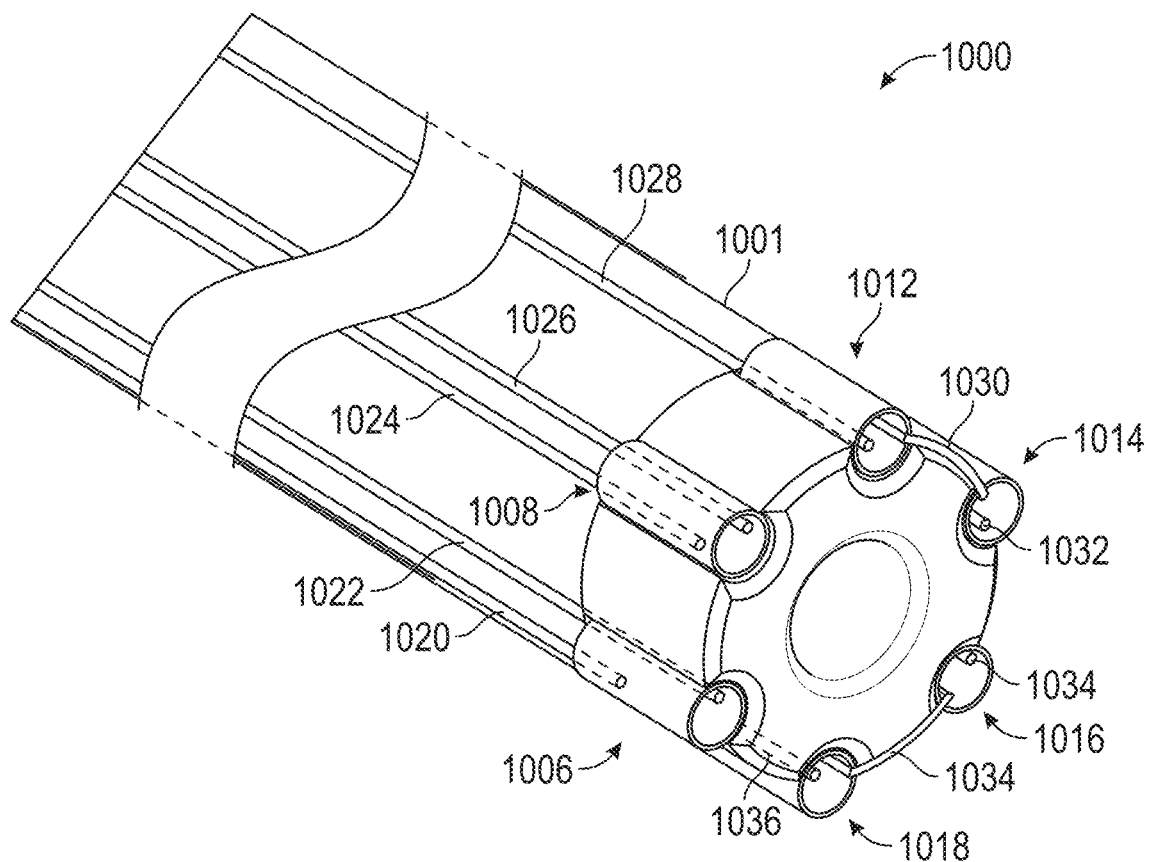
FIG. 10 illustrates an exemplary catheter including shock wave emitters configured to be fired independently from a plurality of shock wave emitters configured to be fired simultaneously.

As described throughout, a plurality of shock wave emitters positioned at the distal end of the catheters described herein may be electrically connected in series such that applying a voltage pulse across two electrodes causes each of the shock wave emitters to generate a shock wave. In some embodiments, one or more shock wave emitters may be configured to fire independently. FIG. 10 illustrates an exemplary catheter 1000 including shock wave emitters 1006 and 1008 configured to fire independently of one another and of the other shock wave emitters 1012, 1014, 1016, and 1018 included on catheter 1000. Shock wave emitter 1006 includes an electrode pair formed by an exposed end of an insulated wire 1022 and a conductive band 1070. The insulated wire 1022 extends into the conductive band 1070 from a proximal end of the conductive band toward a distal end of the conductive band 1070 and is positioned such that the exposed end of the wire 1022 is separated by a spark gap from conductive band 1070. The insulated wire 1022 may extend from the proximal end of the conductive band 1070 along the length of the catheter body 1001 of catheter 1000 to connect to a first terminal of a voltage source. A second insulated wire 1020 may extend into the conductive band 1070 from the proximal end of the band and connect to (e.g., may be soldered, crimped, tapes, clamped, or otherwise connected to) a surface of the conductive band 1070. The second insulated wire may extend from the proximal end of the conductive band 1070 along the length of the catheter body to connect to a second terminal of the voltage source. The insulated wires 1020 and 1022, respectively, may be connected to a negative and positive terminal of the voltage source. Accordingly, when a voltage is applied across wire 1020 and 1022, a shock wave is generated at shock wave emitter 1006, but the voltage applied across wire 1020 and 1022 does not result in shock waves at any of the other shock wave emitters provided on catheter 1000.

Similarly, shock wave emitter 1008 includes an electrode pair formed by an exposed end of an insulated wire 1026 and a conductive band 1072. The insulated wire 1026 extends into the conductive band 1072 from a proximal end of the conductive band toward a distal end of the conductive band 1072 and is positioned such that the exposed end of the wire 1026 is separated by a spark gap from conductive band 1072. The insulated wire 1026 may extend from the proximal end of the conductive band 1072 along the length of the catheter body 1001 of catheter 1000 to connect to a first terminal of a voltage source. A second insulated wire 1024 may extend into the conductive band 1072 from the proximal end of the band and connect to (e.g., may be soldered, crimped, tapes, clamped, or otherwise connected to) a surface of the conductive band 1072. The second insulated wire may extend from the proximal end of the conductive band 1072 along the length of the catheter body to connect to a second terminal of the voltage source. The insulated wires 1026 and 1024, respectively, may be connected to a negative and positive terminal of the voltage source. Accordingly, when a voltage is applied across wire 1024 and 1026, a shock wave is generated at shock wave emitter 1008, but the voltage applied across wire 1024 and 1026 does not result in shock waves at any of the other shock wave emitters provided on catheter 1000. In contrast, the plurality of shock wave emitters 1012, 1014, 1016, and 1018 are electrically connected in series and thus fire simultaneously with one another, for instance, in the same manner described above with reference to the shock wave emitters of catheter 200 illustrated in FIG. 3A.

Constructive interference of the shock waves generated by the shock wave emitters described herein involves the combination/overlap of shock waves produced by each of the respective emitters distally of the distal end of the catheter. The combination of the individual shock waves results in a combined shock wave that has a higher pressure than the shock waves emitted by each individual emitter, which enables the combined shock wave to treat denser and more rigid calcified lesions in the body. FIGS. 11A-11C illustrate constructive interference of shock waves generated by a plurality of shock wave emitters, and how the shape of the catheter body and/or the positioning of the shock wave emitters may affect the direction of shock wave propagation and resulting constructive interference according to some embodiments. In some embodiments, constructive interference of pressure waves may be controlled by syncing or offsetting the timing of delivery of energy pulses to individual emitters.

FIG. 11A illustrates a side view of a catheter 1100a including a plurality of shock wave emitters 1106a-1108a at a distal end of a catheter body 1101. Each of shock wave emitters 1106a-1108a are positioned such that a distal most surface of each shock wave emitter is respectively positioned flush with a flat (i.e., perpendicular to a longitudinal axis of the catheter body 1101) distal most surface 1104a of catheter body 1101. In some embodiments, positioning a distal most surface of the shock wave emitters flush with a flat distal most surface of the catheter body 1101 may result in shock waves from each of the respective emitters that propagate distally of the distal end of the catheter body 1101 along each of the respective longitudinal axes 1109a, 1110a, and 111a, of the plurality of shock wave emitters. The shock waves generated by each of the respective shock wave emitters 1106a-1108a may propagate forward in a unitary direction, as illustrated, and constructively interfere with one another distally of the distal end of the catheter body 1101. More specifically, each shock wave emitter 1106a-1108a may generate a respective shock wave. As each of the shock waves propagate forward distally of the distal end of catheter body 1101, the shock waves expand and begin to overlap with the shock waves generated by each of the other emitters. The overlapping shock waves constructively interfere with one another to form a combined shock wave that continues to propagate forward distally of the distal end of the catheter body 1101. In some embodiments, the combined shock wave propagates distally of the distal end of the catheter body 1101 in the direction of the longitudinal axis 1112a of the catheter body 1101.

FIG. 11B illustrates a side view of a catheter 1100b including a plurality of shock wave emitters 1106b-1108b at a distal end of a catheter body 1101. FIG. 11B illustrates that the shape of the catheter body may be configured to enable directional control of shock waves. In the embodiment of FIG. 11B, a distal most surface 1104b of catheter body 1101 is slanted, rather than perpendicular to a longitudinal axis 1112b of the catheter body 1101 (i.e., configured such that a plane corresponding to the distal most surface 1104b of the catheter body 1101 intersects a plane corresponding to the longitudinal axis 1112b of catheter body 1101 at an angle greater than or less than 90 degrees). The catheter 1100B of FIG. 11B includes a plurality of shock wave emitters 1106b-1108b. The shock wave emitters 1106b-1108b are positioned such that a distal most surface of each shock wave emitter is positioned at a different distal location relative to each of the other shock wave emitters. In the embodiment of FIG. 11B, a distal most surface of shock wave emitter 1106b is positioned at a first location relative to a proximal end (left side of the catheter 1100 from the view of FIG. 11B) of catheter body 1101, a distal most surface of shock wave emitter 1107b is positioned at a second location relative to the distal most surface of shock wave emitter 1106b, and a distal most surface of shock wave emitter 1108b is positioned at a third location relative to the distal most surfaces of both shock wave emitters 1106b and 1107b. Optionally, the distal most surface of each of the shock wave emitters 1106b-1108b may be positioned flush with the distal most surface 1104b of catheter body 1101.

The relative positioning of shock wave emitters 1106b-1108b and the slanted distal most surface of catheter body 1101 may result in shock waves generated by each of the shock wave emitters that propagate distally of the distal end of the catheter body 1101 parallel to one another at an angle diverging from each of their respective longitudinal axes 1109b, 1110b, and 1111b. Thus, the shock waves generated by each of the shock wave emitters 1106b-1108b propagate parallel to one another at the same angle diverging from the longitudinal axis 1112b of the catheter body 1101, and accordingly, the shock waves may constructively interfere with one another and propagate forward in the same direction as the shock waves generated by each of the respective shock wave emitters relative to the longitudinal axis 1112b of catheter body 1101.

FIG. 11C illustrates that the positioning shock wave emitters 1106c-1108c relative to a distal most surface 1104c of the catheter body 1101 (for instance, in a staggered formation relative to a flat distal most surface of catheter body 1101) may enable directional control of shock waves. In the embodiment of FIG. 11C, a distal most surface of shock wave emitter 1106c is positioned flush with a distal most surface 1104c of catheter body 1101, a distal most surface of shock wave emitter 1107c is recessed a first distance from the distal most surface 1104c of catheter body 1101, and a distal most surface of shock wave emitter 1108c is recessed a second distance, greater than the first distance, from the distal most surface 1104c of catheter body 1101.

Shock wave emitter 1106c may produce shock waves that propagate distally of the distal end of the catheter body 1101 along the longitudinal axis 1109c of shock wave emitter 1106c. In contrast, the positioning of shock wave emitters 1107c and 1108c may result in shock waves that propagate distally of the distal end of the catheter body 1101 at respective angles relative to the longitudinal axes 1110c and 1111c of shock wave emitters 1107c and 1108c, such that the shock waves diverge from the longitudinal axes of shock wave emitters 1107c and 1108c. In some embodiments, the recession of the distal most surface of a shock wave emitter further into the catheter body 1101 may result in shock waves that diverge further (i.e., at an angle greater in magnitude) from the longitudinal axis of the respective shock wave emitter. In some embodiments, the shock waves constructively interfere with one another as illustrated and propagate forward at an angle relative to the longitudinal axis 1112c of catheter body 1101, wherein the direction of propagation of the constructively interfering shock waves is based on the respective direction of propagation of the individual shock waves generated by each of the shock wave emitters.

Figure 12A:
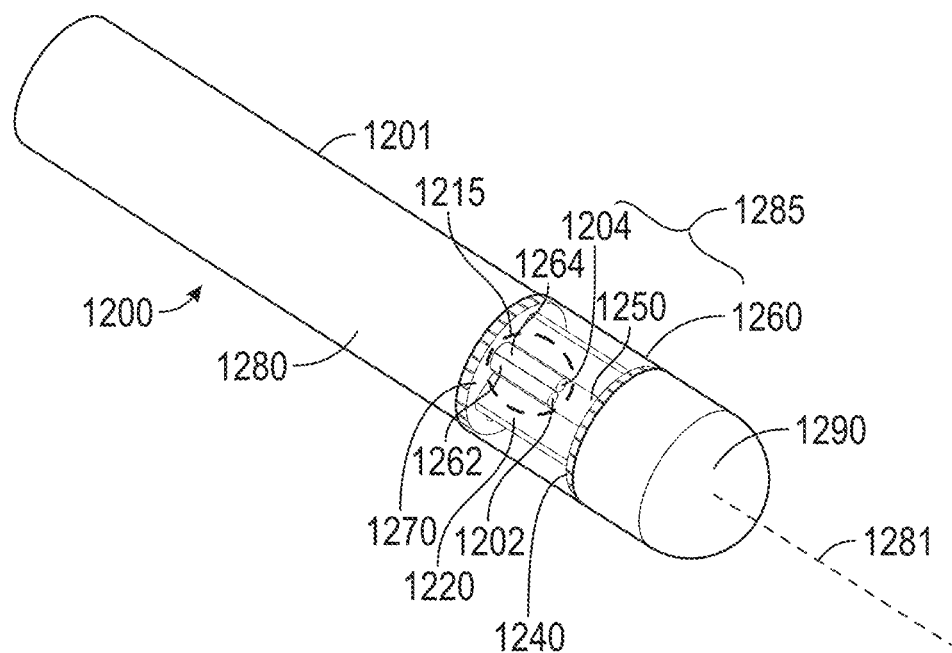
FIGS. 12A-12C illustrate catheters including a plurality of shock wave emitters, according to some embodiments.
Figure 12B:
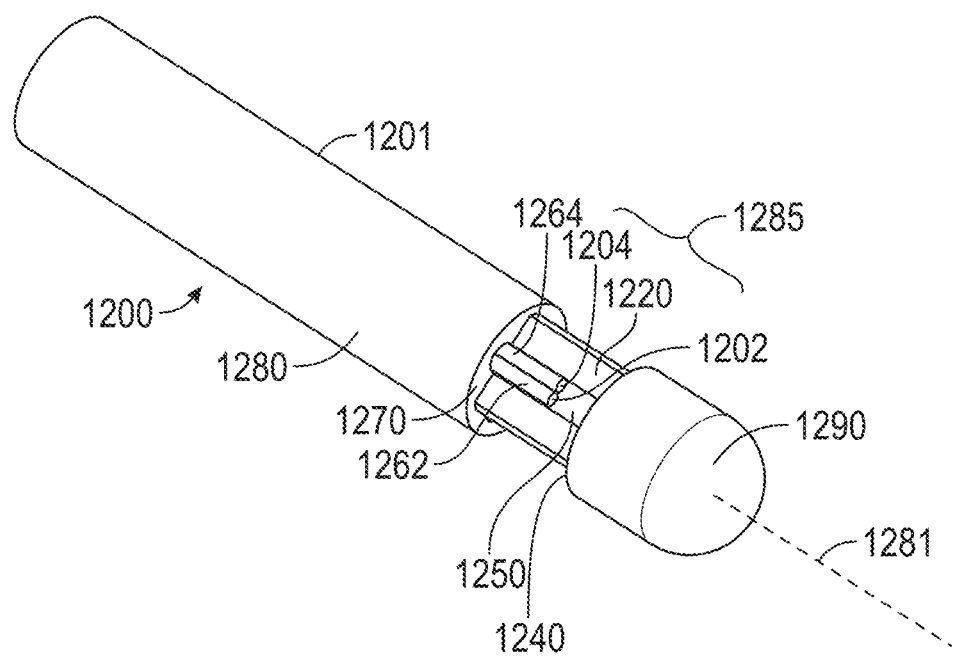
Figure 12C:
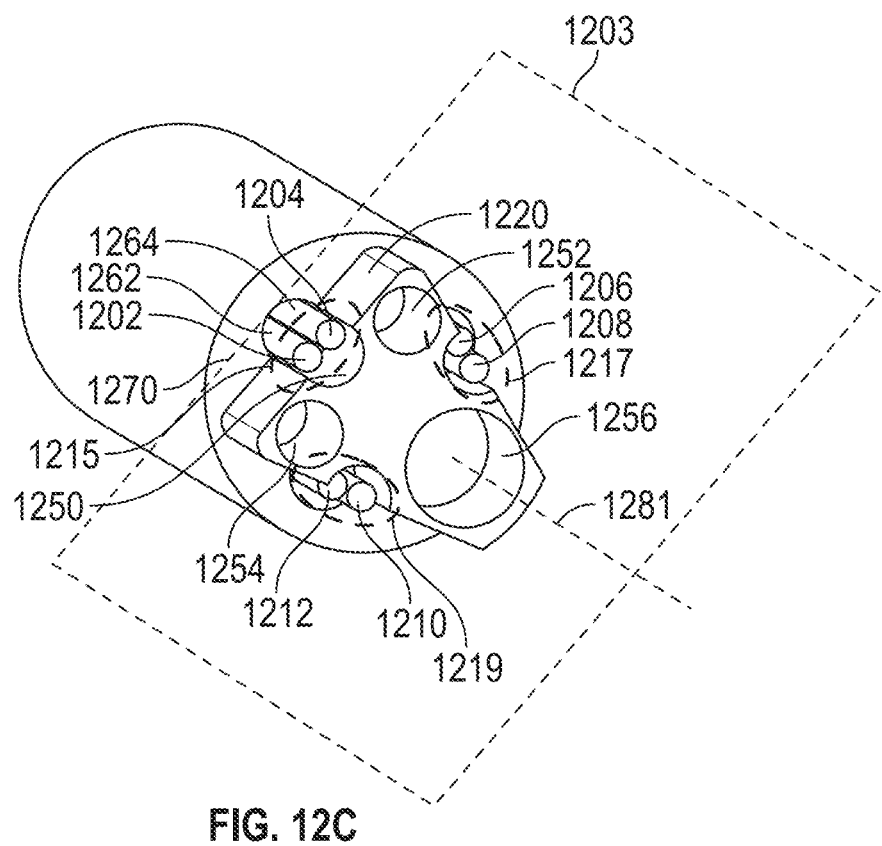

FIGS. 12A-12C illustrate exemplary catheters that include a plurality of shock wave emitters according to some embodiments of the disclosure. In some embodiments, the catheter is configured to emit shock waves in a primarily radial direction (i.e., transverse to a longitudinal axis of the catheter) from a plurality of shock wave emitters. Similar to embodiments described above, the respective shock wave emitters may include an electrode pair defined by ends of a pair of conductive wires separated by a spark gap. However, other configurations (e.g., an electrode pair defined by a wire end and a conductive sheath, emitter band, or other conductive material, such as the configuration illustrated in FIGS. 3A, 3B, and 10 above) are also possible. FIG. 12A illustrates an isometric view of a catheter 1200 that includes a shock wave emitter 1215 that includes pair of electrodes 1202 and 1204 separated by a spark gap. Electrodes 1202 and 1204 are defined by respective ends of first and second conductive wires. The first and second conductive wires 1262 and 1264 may extend along at least a portion of the length of the catheter body 1201 to connect to a positive and negative terminal of a voltage source. When a voltage is applied across the electrodes 1202 and 1204, a shock wave may be generated, as described throughout.

In some embodiments, the pair of electrodes 1202 and 1204 that form shock wave emitter 1215 are positioned adjacent to a surface 1220. In some embodiments, electrodes 1202 and 1204 are positioned within a cavity 1250 of surface 1220. In some embodiments, at least one of the cavity 1250 (e.g., a concave, rectangular, or other carve-out of surface 1220) and surface 1220 are configured to cause shock waves that are generated when a voltage (pulse) is applied across the electrodes 1202 and 1204 to propagate outward from the surface 1220 (e.g., radially from the catheter 1200 with respect to longitudinal axis 1281). In other words, the surface 1220 and/or cavity 1250 may be configured to reflect shock waves generated by the emitter. Accordingly, at least one of the cavity 1250 and surface 1220 may be formed at least in part of a material that at least partially reflects shock waves. The generated shockwaves thus may be at least partially reflected from the surface 1220 and/or cavity 1250, focusing the shockwaves in a radially outward direction from the surface and cavity. In some embodiments, at least a portion of surface 1220 is formed of one of aluminum, nitinol, stainless steel, or an alloy thereof.

In some embodiments, the surface 1220 may be planar, curved, or any other geometry configured to cause shock waves generated by shock wave emitter 1215 to propagate radially outward from the surface 1220. The geometry of the surface may impact the form and manner of propagation of the shock waves. For instance, an angle of tilt of the surface 1220 may enable directional control over shock waves, thus allowing for more targeted treatment. In some embodiments, the magnitude of curvature of the surface 1220 may impact the form of the emitted shock waves. For example, a higher magnitude of curvature of surface 1220 may result in shock waves having a relatively smaller radius, and a lower magnitude of curvature of surface 1220 may result in shock waves having a relatively larger radius.

According to some embodiments, and as illustrated in FIG. 12A, the catheter body 1201 includes a first portion 1280 and a second portion 1290 separated by a chamber 1285. The second portion 1290 may be distal of the shock wave emitter 1215 and may form a distal end of catheter 1200. In some embodiments, at least one of the first portion 1280 and the second portion 1290 of catheter 1200 are formed at least in part of a material that does not readily transmit emitted shock waves. In some embodiments, at least a portion of at least one of the first portion 1280 and the second portion 1290 of catheter 1200 are formed of one of aluminum, nitinol, stainless steel, or an alloy thereof.

In some embodiments, the plurality of shock wave emitters are positioned at least partially within the chamber 1285. The first portion 1280 of catheter body 1201 may include a surface 1270 positioned at a proximal end of chamber 1285, adjacent to the chamber 1285. The second portion 1290 of catheter body 1201 may include a surface 1240 positioned at a distal end of chamber 1285, adjacent to the chamber 1285. The surfaces 1270 and 1240, similarly to the first portion of catheter body 1280 and second portion of the catheter body 1290, may be formed at least in part of a material that does not readily transmit emitted shock waves (e.g., aluminum, nitinol, stainless steel, or an alloy thereof). Accordingly, the surfaces 1270 and 1240 may further impact the shape and manner of propagation of shock waves emitted from shock wave emitter 1215, for instance, by reflecting shock waves at least partially in a longitudinal direction upon contact with surfaces 1270 and 1240 and/or constraining the propagation of the shock waves along the longitudinal axis 1281 of catheter 1200 within the chamber 1285.

In some embodiments, an enclosure 1260 (e.g., an acoustically transparent window) at least partially circumscribes the plurality of shock wave emitters and defines the chamber 1285. In some embodiments, the enclosure 1260 defines an outer diameter of the chamber 1285. The enclosure 1260 facilitates transmission of shock waves from the inner chamber to a target treatment site. For instance, similarly to the enclosure 190 described above, the enclosure/acoustically transparent window 1260 can be filled or inflated by pumping a conductive fluid, such as saline and/or contrast agent into its interior volume. As described above, without an enclosure, cavitation bubbles formed during shock wave generation may exert tensile forces on a target treatment area when they collapse upon impact with the treatment area. However, with enclosure 1260 enclosing the radially firing shock wave emitters, the cavitation bubbles resulting from shock wave generation are separated from the target treatment area. Accordingly, the enclosure can protect soft tissue from potential damage resulting from the cavitation bubbles.

In some embodiments the enclosure 1260 is formed of a thin, acoustically transparent material, such as polyethylene or nylon, which can provide for efficient fluid-to-tissue transmission and effective coupling of the pressure pulse from shock wave emitter to the occlusion or other calcification. In some embodiments, the catheter 1200 may be connected to a fluid source 540 and fluid pump 550 (e.g., as shown in FIG. 5). The fluid pump 550 may fill the interior volume of the enclosure 1260 with fluid to a certain pressure. The conductive fluid may be circulated within the interior volume of the enclosure (e.g., chamber 1285) via a lumen of the catheter 1200, for instance lumen 1252 described below with reference to FIG. 12C, by injecting the fluid into the enclosure 1260 by a fluid pump 550 shown in FIG. 5 and drawing it into a fluid return line (e.g., lumen 1254 described below with reference to FIG. 12C).

In some embodiments, the enclosure 1260 may not be included on catheter 1200, for instance, as shown in FIG. 12B. In some embodiments, if the enclosure 1260 is omitted from catheter 1200, the cavitation stresses resulting from cavitation bubble collapse at the target treatment areas may exert additional force on the treatment area to break up dense calcifications.

FIG. 12C illustrates a detailed isometric cutaway view of an example of catheter 1200 that depicts a plurality of shock wave emitters and exemplary interior features of the example of the catheter body 101. The catheter 1200 may include a plurality of shock wave emitters 1215, 1217, and 1219. Similar to shock wave emitter 1215, shock wave emitter 1217 may include a first electrode 1206 and second electrode 1208 separated from one another by a second spark gap, and shock wave emitter 1219 may include a first electrode 1210 and second electrode 1212 separated from one another by a third spark gap. In some embodiments, the respective electrodes of shock wave emitters 1215, 1217, and 1219 are defined by the exposed distal end of a conductive wire; although, as described throughout, one of the electrodes at each emitter may instead be formed of a conductive sheath, band, or other conductive material. At least two of the wires may respectively extend along the length of the catheter body 1201 to connect to positive and negative terminals of a voltage source. For instance, each of the wires may extend along the length of the catheter body to connect to a respective positive and negative terminal of a voltage source. Accordingly, each of the respective shock wave emitters 1215-1217 may be configured such that it can be fired (e.g., generate shock waves) independently of each of the other shock wave emitters provided on the catheter 1200. In some embodiments, a wire at a first emitter may extend along the length of the catheter to connect to a positive terminal, and a wire at a second emitter may extend along the length of the catheter to connect to a negative terminal, and the remaining wires may connect each of the respective shock wave emitters 1215, 1217, and 1219 in series such that when a voltage is applied across the two wires connected to the voltage source, a shock wave is generated by each of the shock wave emitters 1215, 1217, and 1219, for instance as described above with reference to catheter 100 illustrated in FIG. 1B. In some embodiments, at least two of the shock wave emitters (e.g., emitters 1215 and 1217) may be connected in series, and the remaining emitter (e.g., 1219) may be configured to fire independently of the two connected in series. In some embodiments, the wires may extend into a respective lumen of the catheter body that extends from the chamber 1285 to a proximal end of the catheter body 1201.

Shock wave emitters 1215, 1217, and 1219 may be evenly spaced (positioned at increments of about 120 degrees/circumferentially uniformly distributed about the longitudinal axis) about the longitudinal axis 1281. Although, in some embodiments, as discussed throughout, the 1215, 1217, and 1219 may instead be unevenly spaced (e.g., 1215 and 1217 may be separated by 100 degrees and 1217 and 1219 may be separated by 260 degrees, and so on). For instance, more shock wave emitters may be positioned on one side (e.g., along a dorsal and ventral side of the catheter) than the opposite side. Further, while the catheter 1200 is illustrated as including three shock wave emitters, it should be understood that additional emitters could be included without deviating from the scope of the disclosure.

As illustrated in FIG. 12C, in one or more embodiments, shock wave emitters are generally coplanar with a virtual plane 1203 that is perpendicular to the longitudinal axis 1281 of the catheter. In some embodiments, the shock wave emitters may be positioned at staggered locations along the longitudinal axis, as described throughout. For instance, a first emitter may be positioned distally of a second emitter, a third emitter may be positioned distally of one or both of the first and second emitters, and so on. In various embodiments, shock waves generated by emitters 1215, 1217, and 1219 and emitted from the radially-emitting catheter 1200 may constructively interfere with one another as they propagate outwardly from the catheter 1200, for instance, as described in U.S. Pat. No. 11,779,363, which is incorporated herein by reference in its entirety.

In some embodiments, as illustrated in FIG. 12C, catheter 1200 includes a plurality of lumens, such as lumens 1250, 1252, and 1256 formed into the catheter body 1201. The lumens 1250, 1252, and 1256 may extend along the length of the catheter body 1201 to serve a variety of purposes. For instance, in some embodiments, lumen 1252 may be configured to receive and/or fluidly connect to a fluid supply line and lumen 1254 may be configured to receive and/or fluidly connect to a fluid return line. The lumens may extend to the chamber 1285 such that the chamber can be filled with a conductive fluid to facilitate shock wave transmission. In some embodiments, lumen 1256 may be configured to receive a guide wire, similarly to central lumen 150 described above.

Figure 13A:
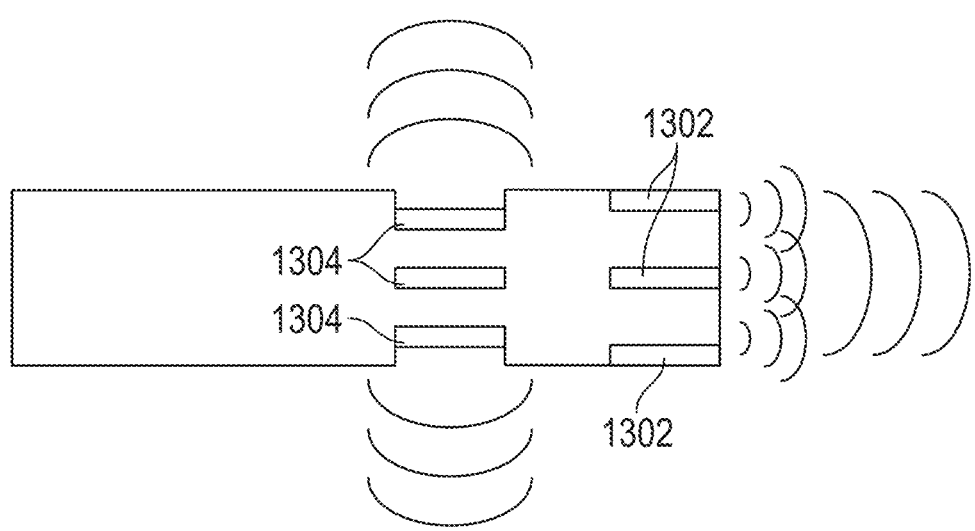
FIGS. 13A and 13B illustrate a catheter including forward firing and side firing shock wave emitters according to some embodiments.
Figure 13B:
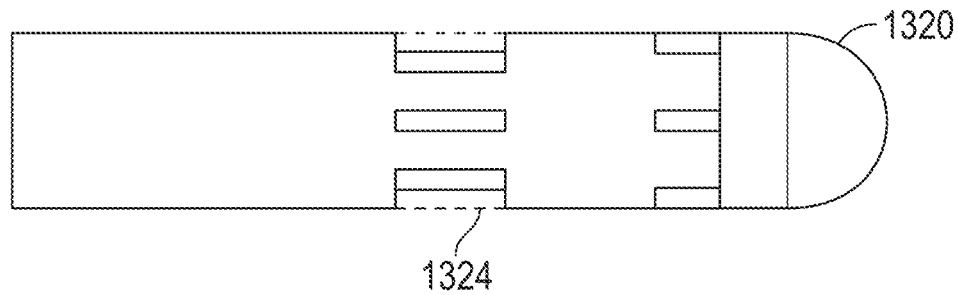

FIGS. 13A and 13B illustrate a catheter 1300 that includes both forward firing and radially firing shock wave emitters, according to some embodiments. Catheter 1300 may include any combination of the features described above with reference to FIGS. 1A-12C. In some embodiments, catheter 1300 includes a first plurality of shock wave emitters 1302 disposed at a distal end of the catheter body. In some embodiments, each shock wave emitter of the plurality of shock wave emitters disposed at a distal end of the catheter body is configured to generate a shock wave that propagates distally of the catheter body. The first plurality of shock wave emitters may include any of the features described above with reference to the shock wave emitters illustrated in FIGS. 1A-11C.

In some embodiments, catheter 1300 also includes a second plurality of shock wave emitters 1304 positioned proximally of the distal end of the catheter body. In some embodiments, each of the second plurality of shock wave emitters are respectively configured to generate shock waves that propagate radially from the catheter body. The second plurality of shock wave emitters 1304 may include any of the features described above with reference to the shock wave emitters illustrated in FIGS. 12A-12C.

In some embodiments, the first plurality of shock wave emitters is configured to generate a first plurality of shock waves 1302 independently of the second plurality of shock wave emitters 1304. In some embodiments, the first plurality of shock wave emitters 1302 may be configured to generate a plurality of shock waves simultaneously with the second plurality of shock wave emitters 1304. In some embodiments, any respective shock wave emitter of both the first plurality of shock wave emitters and the second plurality of shock wave emitters may be configured to generate shock waves independently of any of the other shock wave emitters. Accordingly, a user of catheter 1300 may choose between forward firing, side firing, and/or simultaneous forward and side firing. Further, the user may choose between firing any one of the shock wave emitters individually, firing the first plurality of emitters in unison, firing the second plurality of emitters in unison, firing all emitters in unison, or any combination thereof.

Figure 14:
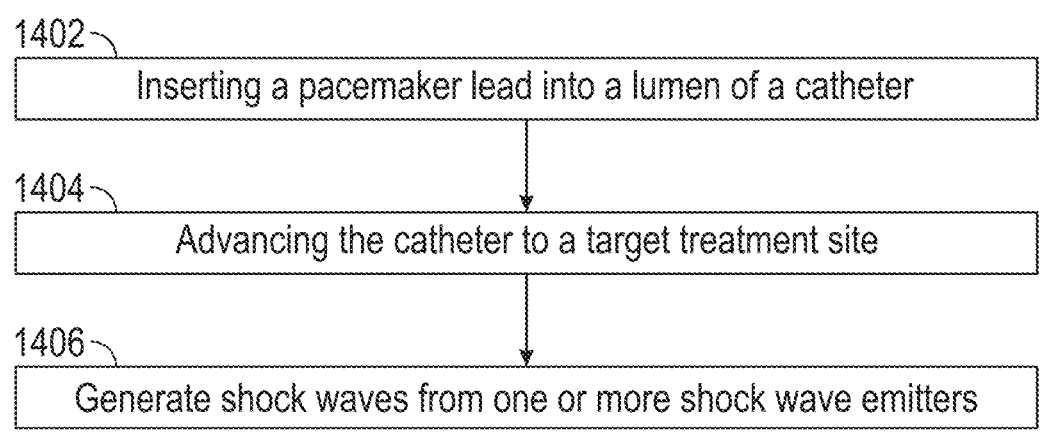
FIG. 14 illustrates a method for pacemaker lead removal according to some embodiments.

As discussed above, catheters according to the principles described herein can be used to facilitate removal of pacemaker leads, which often become encased in fibrotic tissue. FIG. 14 illustrates a method 1400 for using a shock wave catheter for removing a pacemaker lead. Method 1400 may be performed by any of the catheters described herein.

At step 1402, a proximal end of a pacemaker lead is inserted into a central lumen of a shock wave catheter, such as through central lumen 150 of catheter 100, outside of the body. At step 1404, the catheter is advanced into and through vasculature of the body to the target treatment site in the heart, using the pacemaker lead as a guide. The target treatment site may be the location where the pacemaker lead anchors into the heart wall.

At step 1406, one or more shock waves are generated by one or more shock wave emitters of the catheter. Step 1406 may include using one or more forward firing shock wave emitters to break up fibrotic tissue located in front of a distal end of the catheter. At least a portion of the fibrotic tissue encasing the pacemaker lead may be positioned adjacent to the shock wave emitters, such as illustrated in FIG. 9, and the distally propagating shock waves may impinge on the fibrotic tissue, breaking it up.

In some embodiments, the catheter may also include a one or more shock wave emitters positioned proximally of the distal end of the catheter body and configured to generate shock waves that propagate radially from the catheter body, for instance, as described above with reference to FIG. 13. Accordingly, the method 1400 may include generating a plurality of shock waves using the one or more shock wave emitters configured to generate shock waves that propagate radially from the catheter body to at least partially break up a calcified region of vasculature leading to the target site.

It may be desirable to arrange the shock wave emitters and corresponding electrodes such that when the shock wave emitters of a catheter are simultaneously driven, a single cavitation bubble is formed that propagates distally of the distal end of the shock wave emitters (i.e., in contrast to a plurality of relatively smaller cavitation bubbles that may constructively interfere distally of the distal end). This may be accomplished, for instance, as described below with reference to FIG. 15, by configuring the shock wave emitters such that each of the shock wave emitters shares a common electrode. The common electrode may be positioned at a location between each of the other electrodes (e.g., the common electrode may be positioned at a center of a distal end of the catheter and an electrode of each respective shock wave emitter may be positioned at an equal distance from the common electrode about a circumference of the distal end of the catheter).

Figure 15:
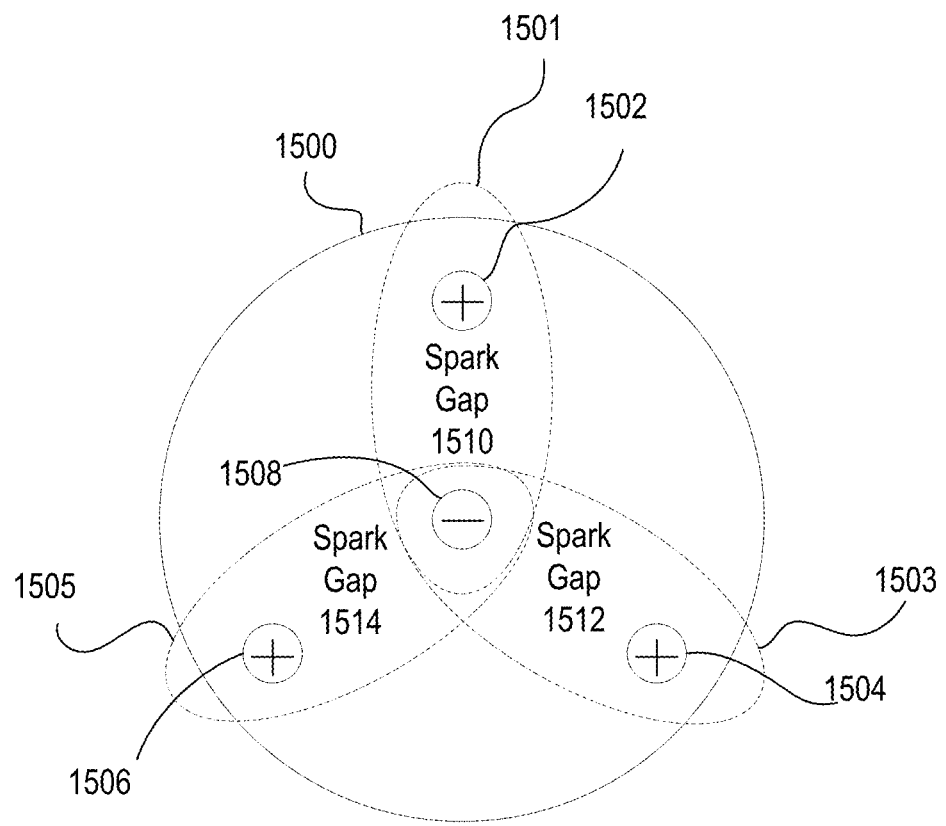
FIG. 15 illustrates a front view of an exemplary catheter 1500 for generating shock waves according to some embodiments.

FIG. 15 illustrates a front view of an exemplary catheter 1500 for generating shock waves according to some embodiments. Catheter 1500 may include a plurality of shock wave emitters 1501, 1503, and 1505. Each of the shock wave emitters 1501, 1503, and 1505 may include a respective electrode 1502, 1504, and 1506 connected to a respective positive terminal (e.g., supply terminal) of a voltage source (e.g., shock wave energy generator 530), for instance, by a supply wire that extends along the length of the catheter 1500. The respective electrodes 1502, 1504, and 1506 of each of shock wave emitters 1501, 1502, and 1503 may be spaced apart by a respective spark gap 1510, 1512, and 1514 from an electrode 1508 that is connected to a negative terminal (e.g., return terminal) of the voltage source. Accordingly, electrode 1508 may form one of the electrodes at each respective shock wave emitter. The respective positive terminals connected to each of electrodes 1502, 1504, and 1506 may be simultaneously pulsed, resulting in a voltage applied across the respective spark gaps 1510, 1512, and 1514 separating each of electrodes 1502, 1504, and 1506 from electrode 1508. The electrodes may be positioned such that when a sufficiently high voltage is applied across the electrodes 1502 and 1508, 1504 and 1508, and 1506 and 1508, each shock wave emitter 1501, 1503, and 1505 generates a shock wave that propagates in a direction forward of the distal end of the catheter body. For instance, electrode 1508 may be positioned at an equal distance from each of electrodes 1502, 1504, and 1506. Electrode 1508 may be positioned at the center of the distal end of catheter 1500, and electrodes 1502, 1504, and 1506 may be positioned at equal distances from electrode 1508 about the circumference of the distal end of the catheter 1500, as shown. Additionally, the shock wave emitters are configured such that when each simultaneously generates a shock wave, a single combined cavitation bubble may be formed rather than three separate cavitation bubbles that constructively interfere distally of the distal end of catheter 1500. The voltage polarity (i.e., direction of current flow) between the respective electrodes of shock wave emitters 1501, 1503, and 1505 may be switched between voltage pulses. Such polarity switching may promote more uniform wear of electrodes and extend device longevity.

Although the electrode assemblies and catheter devices described herein have been discussed primarily in the context of treating coronary occlusions, such as lesions in vasculature, the electrode assemblies and catheters herein can be used for a variety of occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

The elements and features of the exemplary electrode assemblies and catheters discussed above may be rearranged, recombined, and modified, without departing from the present invention. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

It should be noted that the elements and features of the example catheters illustrated throughout this specification and drawings may be rearranged, recombined, and modified without departing from the present invention. For instance, while this specification and drawings describe and illustrate catheters having several example balloon designs, the present disclosure is intended to include catheters having a variety of balloon configurations. The number, placement, and spacing of the electrode pairs of the shock wave generators can be modified without departing from the subject invention. Further, the number, placement, and spacing of balloons of catheters can be modified without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

While this disclosure has been particularly shown and described with references to embodiments thereof, it will be understood by those skilled in the art that various changes in form and details may be made therein without departing from the scope of the claims. For all of the embodiments described above, the steps of the methods need not be performed sequentially.

The invention claimed is:

1. A catheter for use in a body lumen, the catheter comprising:
    a catheter body; and
    a plurality of shock wave emitters disposed at a distal end of the catheter body, each shock wave emitter configured to generate a shock wave that propagates distally of the catheter body, wherein at least one shock wave emitter of the plurality of shock wave emitters comprises electrodes separated by a spark gap and at least one electrical connection to an electrode of at least one other shock wave emitter of the plurality of shock wave emitters, wherein an outermost surface of a shock wave emitter of the plurality of shock wave emitters is positioned externally relative an outer circumferential surface of the catheter body.

2. The catheter of claim 1, wherein the plurality of shock wave emitters are arranged such that shock waves emitted from the plurality of shock wave emitters can constructively interfere distally of the catheter body.

3. The catheter of claim 1, wherein the plurality of shock wave emitters are electrically connected in series such that an electrical pulse applied across an electrode of a first shock wave emitter of the plurality of shock wave emitters and an electrode at a second shock wave emitter of the plurality of shock wave emitters causes each of the plurality of shock wave emitters to emit a respective shock wave.

4. The catheter of claim 1, wherein at least one shock wave emitter of the plurality of shock wave emitters can be driven independently of at least a second shock wave emitter of the plurality of shock wave emitters.

5. The catheter of claim 1, wherein a first shock wave emitter of the plurality of shock wave emitters comprises an exposed distal tip of a first insulated wire and an exposed distal tip of a second insulated wire, the second insulated wire extending to a second shock wave emitter of the plurality of shock wave emitters.

6. The catheter of claim 5, wherein the first insulated wire extends along the length of the catheter body and is positioned within a lumen of the catheter body.

7. The catheter of claim 1, wherein a first shock wave emitter of the plurality of shock wave emitters comprises an exposed distal end of an insulated wire and a conductive emitter band that is separated from the exposed distal end of the insulated wire by a spark gap.

8. The catheter of claim 1, wherein the plurality of shock wave emitters comprises at least three shock wave emitters.

9. The catheter of claim 1, wherein the plurality of shock wave emitters are arrayed symmetrically about a longitudinal axis of the catheter body.

10. The catheter of claim 1, wherein a distal most surface of a shock wave emitter of the plurality of shock wave emitters is flush with a distal most surface of the distal end of the catheter body.

11. The catheter of claim 1, wherein a distal most surface of a shock wave emitter of the plurality of shock wave emitters is recessed from a distal most surface of the distal end of the catheter body.

12. The catheter of claim 1, wherein a distal most surface of a shock wave emitter of the plurality of shock wave emitters is positioned forward of a distal most surface of the distal end of the catheter body.

13. The catheter of claim 1, wherein the plurality of shock wave emitters are disposed at the same distal location relative to the distal end of the catheter body.

14. The catheter of claim 1, further comprising an enclosure positioned to cover the plurality of shock wave emitters at the distal end of the catheter body.

15. The catheter of claim 1, further comprising a central lumen extending from the proximal end of the catheter to the distal end of the catheter.

16. The catheter of claim 15, wherein the central lumen is configured to receive a guide wire or a pacemaker wire lead.

17. The catheter of claim 1, wherein the catheter body comprises an aspiration lumen.

18. The catheter of claim 1, wherein the plurality of shock wave emitters are respectively spaced apart from one another by a distance of between 1 mm and 10 mm.

19. A method for removing a pacemaker lead comprising:
advancing a catheter along the pacemaker lead to a target site comprising fibrotic tissue, the catheter comprising a catheter body and a plurality of shock wave emitters disposed at a distal end of the catheter body, each shock wave emitter configured to generate a shock wave that propagates distally of the catheter body, wherein at least one shock wave emitter of the plurality of shock wave emitters comprises electrodes separated by a spark gap and at least one electrical connection to an electrode of at least one other shock wave emitter of the plurality of shock wave emitters; and
generating one or more shock waves to at least partially break up the fibrotic tissue so that the pacemaker lead can be removed.

20. The method of claim 19, wherein the target site is within the heart.

21. The method of claim 19, wherein the fibrotic tissue is located distally of the distal end of the catheter.

22. The method of claim 19, wherein the pacemaker lead is inserted into a lumen of the catheter to guide the catheter to the target site.

23. The method of claim 19, further comprising: advancing the catheter further along the pacemaker lead to the target site; and generating one or more additional shock waves.

24. The method of claim 19, wherein the catheter further comprises a plurality of shock wave emitters positioned proximally of the distal end of the catheter body, wherein the second plurality of shock wave emitters are respectively configured to generate shock waves that propagate radially from the catheter body; and wherein the method further comprises:
generating a plurality of shock waves that propagate radially of the catheter using the second plurality of shock wave emitters to at least partially break up a calcified region of vasculature leading to the target site.

25. The method of claim 19, wherein the plurality of shock wave emitters are electrically connected to a shock wave energy generator configured to deliver high voltage pulses to at least one shock wave emitter of the plurality of shock wave emitters.

26. The method of claim 25, wherein the high voltage pulses are between 3 k V and 20 kV, including 3 kV and 20 kV.

27. The method of claim 25, wherein the shock wave energy generator is configured to deliver the voltage pulses at a rate of up to 20 Hz, including 20 Hz.

28. The method of claim 25, wherein the shock wave energy generator applies an alternating current to the electrodes to induce a change in the polarity of the electrodes.

29. The method of claim 19, wherein the plurality of shock wave emitters are arranged such that shock waves emitted from the plurality of shock wave emitters can constructively interfere distally of the catheter body.

30. The method of claim 19, wherein at least one shock wave emitter of the plurality of shock wave emitters can be driven independently of at least a second shock wave emitter of the plurality of shock wave emitters.

31. The method of claim 19, wherein the plurality of shock wave emitters comprises at least three shock wave emitters.

32. The method of claim 19, wherein the plurality of shock wave emitters are arrayed symmetrically about a longitudinal axis of the catheter body.

33. A catheter for use in a body lumen, the catheter comprising:
a catheter body; and
a plurality of shock wave emitters disposed at a distal end of the catheter body, each shock wave emitter configured to generate a shock wave that propagates distally of the catheter body, wherein at least one shock wave emitter of the plurality of shock wave emitters comprises electrodes separated by a spark gap, wherein a distal most surface of a shock wave emitter of the plurality of shock wave emitters is flush with a distal most surface of the distal end of the catheter body, and at least one electrical connection to an electrode of at least one other shock wave emitter of the plurality of shock wave emitters.

34. The catheter of claim 33, wherein the plurality of shock wave emitters are arranged such that shock waves emitted from the plurality of shock wave emitters can constructively interfere distally of the catheter body.

35. The catheter of claim 33, wherein the plurality of shock wave emitters are electrically connected in series such that an electrical pulse applied across an electrode of a first shock wave emitter of the plurality of shock wave emitters and an electrode at a second shock wave emitter of the plurality of shock wave emitters causes each of the plurality of shock wave emitters to emit a respective shock wave.

36. The catheter of claim 33, wherein at least one shock wave emitter of the plurality of shock wave emitters can be driven independently of at least a second shock wave emitter of the plurality of shock wave emitters.

37. The catheter of claim 33, wherein a first shock wave emitter of the plurality of shock wave emitters comprises an exposed distal tip of a first insulated wire and an exposed distal tip of a second insulated wire, the second insulated wire extending to a second shock wave emitter of the plurality of shock wave emitters.

38. The catheter of claim 33, wherein a first shock wave emitter of the plurality of shock wave emitters comprises an exposed distal end of an insulated wire and a conductive emitter band that is separated from the exposed distal end of the insulated wire by a spark gap.

39. The catheter of claim 33, wherein the plurality of shock wave emitters comprises at least three shock wave emitters.

40. The catheter of claim 33, wherein the plurality of shock wave emitters are arrayed symmetrically about a longitudinal axis of the catheter body.

41. The catheter of claim 33, wherein the plurality of shock wave emitters are disposed at the same distal location relative to the distal end of the catheter body.

42. The catheter of claim 33, further comprising an enclosure positioned to cover the plurality of shock wave emitters at the distal end of the catheter body.

43. The catheter of claim 33, further comprising a central lumen extending from the proximal end of the catheter to the distal end of the catheter.

44. The catheter of claim 43, wherein the central lumen is configured to receive a guide wire or a pacemaker wire lead.

45. The catheter of claim 33, wherein the catheter body comprises an aspiration lumen.

46. The catheter of claim 33, wherein the plurality of shock wave emitters are respectively spaced apart from one another by a distance of between 1 mm and 10 mm.

47. A catheter for use in a body lumen, the catheter comprising:
a catheter body; and
a plurality of shock wave emitters disposed at a distal end of the catheter body, each shock wave emitter configured to generate a shock wave that propagates distally of the catheter body, wherein at least one shock wave emitter of the plurality of shock wave emitters comprises electrodes separated by a spark gap, wherein a distal most surface of a shock wave emitter of the plurality of shock wave emitters is positioned forward of a distal most surface of the distal end of the catheter body, and at least one electrical connection to an electrode of at least one other shock wave emitter of the plurality of shock wave emitters.

48. The catheter of claim 47, wherein the plurality of shock wave emitters are arranged such that shock waves emitted from the plurality of shock wave emitters can constructively interfere distally of the catheter body.

49. The catheter of claim 47, wherein the plurality of shock wave emitters are electrically connected in series such that an electrical pulse applied across an electrode of a first shock wave emitter of the plurality of shock wave emitters and an electrode at a second shock wave emitter of the plurality of shock wave emitters causes each of the plurality of shock wave emitters to emit a respective shock wave.

50. The catheter of claim 47, wherein at least one shock wave emitter of the plurality of shock wave emitters can be driven independently of at least a second shock wave emitter of the plurality of shock wave emitters.

51. The catheter of claim 47, wherein a first shock wave emitter of the plurality of shock wave emitters comprises an exposed distal tip of a first insulated wire and an exposed distal tip of a second insulated wire, the second insulated wire extending to a second shock wave emitter of the plurality of shock wave emitters.

52. The catheter of claim 51, wherein the first insulated wire extends along the length of the catheter body and is positioned within a lumen of the catheter body.

53. The catheter of claim 47, wherein a first shock wave emitter of the plurality of shock wave emitters comprises an exposed distal end of an insulated wire and a conductive emitter band that is separated from the exposed distal end of the insulated wire by a spark gap.

54. The catheter of claim 47, wherein the plurality of shock wave emitters comprises at least three shock wave emitters.

55. The catheter of claim 47, wherein the plurality of shock wave emitters are arrayed symmetrically about a longitudinal axis of the catheter body.

56. The catheter of claim 47, wherein the plurality of shock wave emitters are disposed at the same distal location relative to the distal end of the catheter body.

57. The catheter of claim 47, further comprising an enclosure positioned to cover the plurality of shock wave emitters at the distal end of the catheter body.

58. The catheter of claim 47, further comprising a central lumen extending from the proximal end of the catheter to the distal end of the catheter.

59. The catheter of claim 58, wherein the central lumen is configured to receive a guide wire or pacemaker lead.

60. The catheter of claim 47, wherein the catheter body comprises an aspiration lumen.

61. The catheter of claim 47, wherein the plurality of shock wave emitters are respectively spaced apart from one another by a distance of between 1 mm and 10 mm.

* * * * *